United States Patent
Moyer

(10) Patent No.: US 12,207,910 B1
(45) Date of Patent: *Jan. 28, 2025

(54) SYSTEMS, METHODS, AND APPARATUSES FOR ANALYZING GALVANIC SKIN RESPONSE BASED ON EXPOSURE TO ELECTROMAGNETIC AND MECHANICAL WAVES

(71) Applicant: Kimchi Moyer, Cos Cob, CT (US)

(72) Inventor: Kimchi Moyer, Cos Cob, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 18/143,667

(22) Filed: May 5, 2023

Related U.S. Application Data

(63) Continuation of application No. 16/831,027, filed on Mar. 26, 2020, now Pat. No. 11,642,039, which is a continuation-in-part of application No. 16/678,121, filed on Nov. 8, 2019, now Pat. No. 11,642,038.

(60) Provisional application No. 62/829,313, filed on Apr. 4, 2019, provisional application No. 62/758,599, filed on Nov. 11, 2018.

(51) Int. Cl.
*A61B 5/00* (2006.01)
*A61B 5/0533* (2021.01)

(52) U.S. Cl.
CPC .......... *A61B 5/0533* (2013.01); *A61B 5/0022* (2013.01); *A61B 5/0048* (2013.01); *A61B 5/0053* (2013.01); *A61B 5/4845* (2013.01); *A61B 5/4848* (2013.01); *A61B 5/4875* (2013.01); *A61B 5/7264* (2013.01)

(58) Field of Classification Search
CPC ... A61B 5/0533; A61B 5/0022; A61B 5/4875; A61B 5/6825; A61B 5/6829; A61B 5/6843; A61B 5/7264; A61B 5/742; A61B 5/7475; A61B 5/748; A61B 2562/0215; A61B 2562/0219; A61B 2562/0247; A61B 2562/08

See application file for complete search history.

(56) References Cited

U.S. PATENT DOCUMENTS

| | | | | |
|---|---|---|---|---|
| 4,683,891 | A * | 8/1987 | Cornellier | G16H 40/63 600/480 |
| 5,676,138 | A * | 10/1997 | Zawilinski | A61B 3/113 600/301 |
| 5,830,140 | A | 11/1998 | Dillinger et al. | |
| 6,167,299 | A * | 12/2000 | Galchenkov | A61N 1/06 600/547 |
| 6,743,182 | B2 * | 6/2004 | Miller | A61B 5/01 600/300 |
| 6,762,609 | B2 * | 7/2004 | Alanen | A61B 5/443 324/689 |
| 7,613,510 | B2 | 11/2009 | Rentea et al. | |
| 7,693,579 | B2 * | 4/2010 | Hindinger | A61H 39/002 607/46 |
| 7,937,139 | B2 | 5/2011 | Horne et al. | |
| 8,099,159 | B2 | 1/2012 | Cook | |

(Continued)

*Primary Examiner* — May A Abouelela
(74) *Attorney, Agent, or Firm* — NEO IP

(57) ABSTRACT

Systems, methods, apparatus, and non-transitory computer readable media for measuring and analyzing galvanic skin response. Responses to stimuli including electromagnetic waves and mechanical waves, as well as substances exposed to electromagnetic waves and mechanical waves, are recorded and analyzed. Electromagnetic waves and mechanical waves are constructed based on biological outputs in one embodiment.

20 Claims, 13 Drawing Sheets

(56) References Cited

U.S. PATENT DOCUMENTS

| | | | |
|---|---|---|---|
| 8,131,355 B2* | 3/2012 | Clark | A61B 5/0531 600/547 |
| 8,332,027 B2* | 12/2012 | Larsen | A61H 39/002 600/548 |
| 8,682,425 B2 | 3/2014 | Larsen et al. | |
| 9,330,680 B2 | 5/2016 | Kassam et al. | |
| 9,788,794 B2* | 10/2017 | LeBoeuf | A61B 5/7239 |
| 9,888,884 B2 | 2/2018 | Chafe et al. | |
| 9,922,286 B1 | 3/2018 | Hazard | |
| 10,130,311 B1* | 11/2018 | De Sapio | A61B 5/7455 |
| 11,089,999 B1* | 8/2021 | Williams | A61B 5/4875 |
| 11,213,218 B2* | 1/2022 | Penning De Vries | G01N 27/041 |
| 2002/0059247 A1 | 5/2002 | Dillinger et al. | |
| 2004/0087838 A1* | 5/2004 | Galloway | G16H 40/63 600/300 |
| 2004/0143170 A1* | 7/2004 | DuRousseau | A61B 5/164 600/595 |
| 2005/0154264 A1* | 7/2005 | Lecompte | A61B 5/4884 128/920 |
| 2008/0077434 A1 | 3/2008 | Man et al. | |
| 2010/0222697 A1* | 9/2010 | Larsen | A61H 39/002 600/548 |
| 2011/0087337 A1* | 4/2011 | Forsell | A61N 1/37247 600/38 |
| 2015/0230726 A1 | 8/2015 | Greaves | |
| 2016/0066859 A1* | 3/2016 | Crawford | A61B 5/681 600/595 |
| 2017/0007847 A1 | 1/2017 | Gross et al. | |
| 2017/0105662 A1* | 4/2017 | Silawan | A61B 5/14542 |
| 2017/0164876 A1* | 6/2017 | Hyde | A61B 5/1118 |
| 2017/0196497 A1* | 7/2017 | Ray | G06N 7/01 |
| 2017/0238812 A1* | 8/2017 | Atlas | A61B 5/747 |
| 2017/0251967 A1* | 9/2017 | Premsukh | A61B 5/0004 |
| 2017/0273574 A1* | 9/2017 | Wu | A61B 5/02055 |
| 2017/0296121 A1* | 10/2017 | Dar | A61N 1/0484 |
| 2017/0322679 A1* | 11/2017 | Gordon | G06F 3/013 |
| 2017/0367614 A1* | 12/2017 | Zuckerman-Stark | A61B 5/02055 |
| 2018/0032126 A1* | 2/2018 | Liu | G06V 10/143 |
| 2018/0042813 A1 | 2/2018 | Chiang | |
| 2018/0085000 A1* | 3/2018 | Weffers-Albu | A61B 5/7282 |
| 2018/0121733 A1* | 5/2018 | Joshi | G06V 20/46 |
| 2018/0184735 A1* | 7/2018 | Longinotti-Buitoni | A61B 5/282 |
| 2018/0228434 A1* | 8/2018 | Dwarika | A61B 5/6801 |
| 2018/0229674 A1* | 8/2018 | Heinrich | A61B 5/18 |
| 2018/0314858 A1* | 11/2018 | Bertrand | G06F 21/64 |
| 2019/0064344 A1* | 2/2019 | Turner | G08B 21/02 |
| 2019/0175097 A1* | 6/2019 | Cowie | A61B 5/01 |
| 2019/0231249 A1* | 8/2019 | Dascalu | A61B 5/746 |
| 2019/0357831 A1* | 11/2019 | Avegliano | G16H 40/63 |
| 2019/0369728 A1* | 12/2019 | Rogers | G06T 19/006 |
| 2020/0138377 A1* | 5/2020 | Huijbregts | A61B 5/681 |
| 2020/0245869 A1* | 8/2020 | Sivan | G06N 3/08 |
| 2020/0288999 A1* | 9/2020 | Lasarov | A61B 5/0006 |
| 2021/0127975 A1* | 5/2021 | Rogers | A61B 5/0205 |
| 2021/0128055 A1* | 5/2021 | Bock | A61B 5/443 |
| 2021/0169425 A1* | 6/2021 | Dirkes | A61B 5/7221 |
| 2022/0100282 A1* | 3/2022 | Nocon | A63F 13/428 |

* cited by examiner

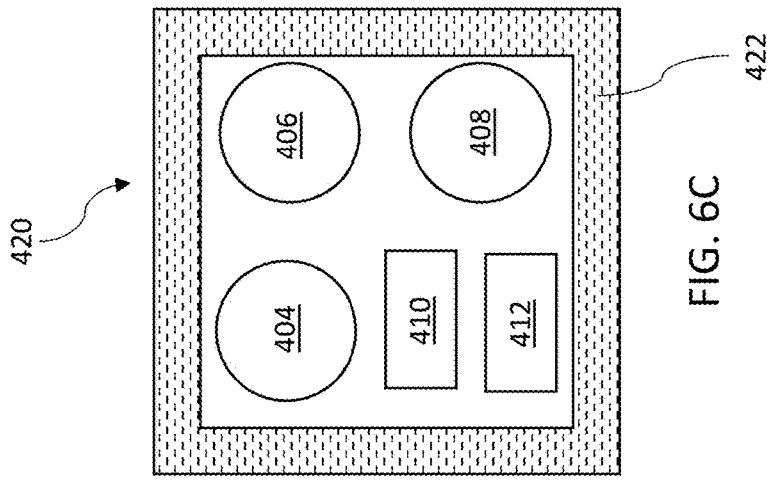
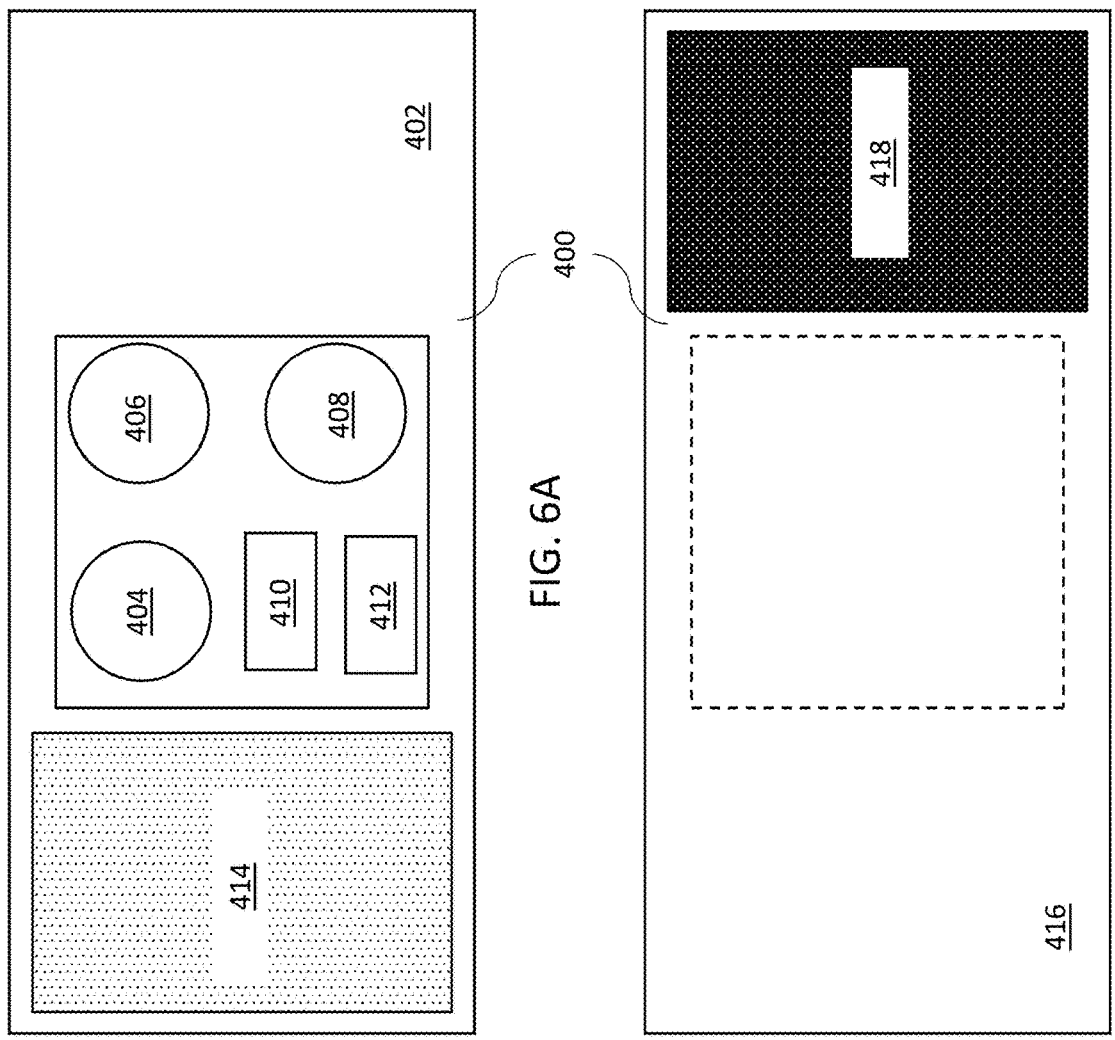

SYSTEMS, METHODS, AND APPARATUSES FOR ANALYZING GALVANIC SKIN RESPONSE BASED ON EXPOSURE TO ELECTROMAGNETIC AND MECHANICAL WAVES

CROSS REFERENCES TO RELATED APPLICATIONS

This application is related to and claims priority from the following US patents and patent applications. This application is a continuation of U.S. application Ser. No. 16/831,027, filed Mar. 26, 2020, which claims the benefit of and priority to U.S. Provisional Application No. 62/829,313, filed Apr. 4, 2019, each of which is incorporated herein by reference in its entirety. U.S. application Ser. No. 16/831,027, filed Mar. 26, 2020, is also a continuation-in-part of U.S. application Ser. No. 16/678,121 filed Nov. 8, 2019, which claims the benefit of U.S. Provisional Patent Application No. 62/758,599, filed Nov. 11, 2018, each of which is incorporated herein by reference in its entirety.

BACKGROUND OF THE INVENTION

1. Field of the Invention

The present invention relates to devices, methods, and systems for measuring galvanic skin response based on exposure to stimuli including electromagnetic waves and mechanical waves and substances exposed to electromagnetic waves and mechanical waves.

2. Description of the Prior Art

It is generally known in the prior art to expose subjects to light and/or sound as part of a therapeutic process. It is also generally known to alter the structure of substances using energy including light and/or sound. Methods and systems for measuring galvanic skin response are also known. One application of galvanic skin response is to measure electrical properties of acupuncture points. Dr. Reinhard Voll, a German physician and engineer, developed a method of measuring galvanic skin response known as Electroacupuncture According to Voll (EAV) in the 1940s.

Representative prior art patent documents include the following:

U.S. Pat. No. 5,830,140 for apparatus and method for registering substance-specific and organism-specific energetic information by inventors Dillinger, et al., filed Nov. 22, 1995 and issued Nov. 3, 1998, is directed to substance-specific and body-specific information in the form of electromagnetic noise stored after separation with bandpass filters so that individual noise spectra segments can reflect the different planes of the body system and stored information of this type can be combined with a carrier and used for therapy or used directly to activate an alcohol/water mixture and produce a homeopathic medicament.

U.S. Publication No. 20020059247 for method of and apparatus for registering and reproducing homeopathic information by inventors Dillinger, et al., filed Jun. 28, 2001 and published May 16, 2002, is directed to homeopathic information in the form of electromagnetic spectra or combinations of spectra or spectra sums downloaded through a global communication network from a site to a terminal and are used to produce homeopathic medicaments or test substances or for treatment of the patient. The homeopathic data is stored and reproduced by music storage and communication formats, especially MP3.

U.S. Pat. No. 9,330,680 for Biometric-music interaction methods and systems by inventors Kassam, et al., filed Sep. 9, 2013 and issued May 3, 2016, is directed to a system and method for the automatic, procedural generation of musical content in relation to biometric data. The systems and methods use a user's device, such as a cell phone to capture image data of a body part, and derive a biometric signal from the image data. The biometric signal includes biometric parameters, which are used by a music generation engine to generate music. The music generation can also be based on user-specific data and quality data related to the biometric detection process.

U.S. Publication No., 20170007847 for Bioresonance frequency emitting device, system, and method by inventors Gross, et al., filed Jul. 7, 2016 and published Jan. 12, 2017, is directed to a phototherapy or BRT process and apparatus, which, using a pre-recorded bioresonance frequency or compilation of frequencies, causes an EMR emitter to emit within a biological window of a target organism to positively or negatively affect the organism. The EMR may be generated in one or more LEDs by a device connected to a controller of the EMR emitter which device provides the pre-recorded bioresonance frequency or compilation of frequencies to control the LEDs' emitted light in terms of its intensity and/or a frequency or flicker-rate.

U.S. Pat. No. 9,888,884 for Method of sonifying signals obtained from a living subject by inventors Chafe, et al., filed Dec. 1, 2014 and issued Feb. 13, 2018, is directed to a digital processor system that obtains at least one time-domain signal representing brain activity and at least one time-domain signal representing heart activity, each having a time-varying signal value. The system produces representations of a plurality of acoustic signals, each of which corresponds to a respective time-domain signal and is produced by concurrently generating a plurality of acoustic parameters, including a plurality of time-varying acoustic parameters. One or more of the plurality of time-varying acoustic parameters is modulated in accordance with at least the signal value of the respective time-domain signal. Each representation of an acoustic signal of the plurality of acoustic signals is further produced by combining the concurrently generated plurality of acoustic parameters to produce the representation of the acoustic signal corresponding to the respective time-domain signal. The system combines the representations of each of the plurality of acoustic signals to produce a combined acoustic signal.

U.S. Publication No. 20040087838 for meridian linking diagnostic and treatment system and method for treatment of manifested and latent maladies using the same by inventors Galloway, et al., filed Jul. 22, 2003 and published May 6, 2004, is directed to a computerized meridian linking diagnostic and treatment system that offers a new paradigm for practitioners in the EAV, GSR, EDS, and Meridian Stress Assessment fields. During the entire procedure, the present invention system outputs two permanent filters (frequencies) that link all of the body's meridians and stabilizes the data access points used for testing and carrying out the many functions of the present invention. The result is an interconnected meridian network linking the internal body systems to the data access points utilized by the system. The process begins by taking energetic readings at data access points. The computer stores the points that are the most stable. After the stable points are obtained, customized filters (frequencies) relating to specific issues or maladies (such as chemical toxins, allergies, digestion, etc.) are output or broadcast.

Using only a single, but stable data access point as a reference point, if any of these filters creates a disturbance to any energetic component, cellular component, tissue, organ, or system of the body, each of which are linked by the interconnected meridian network, an imbalanced reading on the previously stable data access point will be created. The system will then automatically load products (remedies) that are useful for restoring homeostasis or balance. Each of the remedies are stored in the system database and can easily and quickly be scanned through until one or more products or remedies are discovered that will remove the underlying disturbance and allow the patient to obtain an improved level of health. The product/remedy is then placed in a holding tank that stores the results of each test. Specifically, the holding tank stores the filter(s) that created an imbalance/disturbance, the products (remedies) that allow the individual's body to restore homeostasis, balance, or improved health, and various prescription constraints that dictate administration of the products to the patient. The present invention also features several computer software functions, along with various methods of diagnosing maladies and treating a patient using an alternative medicine technique similar to a meridian stress assessment.

U.S. Publication No. 20080077434 for system and method for administration of on-line healthcare by inventors Man, et al., filed Jul. 15, 2005 and published Mar. 27, 2008, is directed to a healthcare administration system useful for the management of anamnesis and medical records, data analysis, guided diagnosis, medical treatment, and clinical investigation. The novel system comprising: a plurality of self-sufficient subsystems adapted to record, store, share, clinically investigate and analyze information by means of a common medical information protocol (CMIP); at least one end-unit device adapted to diagnose and/or treat patients, in communication with a subsystem for controlling, monitoring and recording the treatment process and its outcome by means of a medical protocol; at least one module adapted for a CMIP. The end-unit device is guided by the CMIP so that anamnesis, diagnosis and targeted treatment is dictated, provided, monitored, recorded and/or clinically investigated. The present invention also discloses a guided method for a healthcare administration system, useful for the management of medical records, data analysis, diagnosis, guided treatment and medical investigation by means of the medical system as defined above.

U.S. Pat. No. 7,613,510 for biofeedback device displaying results on a cellular phone display by inventors Rentea, et al., filed Dec. 11, 2003 and issued Nov. 3, 2009, is directed to biofeedback information measured at a body part of a user. The information is communicated to a cellular telephone device and used to produce a display on a display screen of the cellular telephone device.

U.S. Pat. No. 7,937,139 for systems and methods of utilizing electrical readings in the determination of treatment by inventors Home, et al., filed Jul. 20, 2004 and issued May 3, 2011, is directed to a system for determining treatment options from at least two electrical readings. The electrical readings are conductivity measurements of a particular region on the human body. The system utilizes a correlation algorithm to determine the diagnosis which can easily be correlated with appropriate treatments. The correlation algorithm may include the analysis of multiple electrical readings in determining the diagnosis. The system may also utilize a database of clinical data to further assist in determining the diagnosis.

U.S. Pat. No. 8,099,159 for methods and devices for analyzing and comparing physiological parameter measurements by inventor Cook, filed Sep. 13, 2006 and issued Jan. 17, 2012, is directed to methods and devices that are capable of measuring physiological parameters of at least two contact points and determining whether the measured parameters reflect favorable or unfavorable physiological responses are disclosed herein. Specifically, the present invention encompasses a method that can non-invasively monitor physiological parameters of at least two contact points before and after a stimulus is applied to a subject and compare the measured parameters to determine whether the physiological state of the subject is favorable or unfavorable.

U.S. Pat. No. 8,131,355 for automated skin electrical resistance measurement device and method by inventor Clark, filed Aug. 1, 2007 and issued Mar. 6, 2012, is directed to an automated skin resistance measurement device having an applied signal selector for selecting one or more applied signal forms from an applied signal library, an applied signal generator in communication with the applied signal selector for generating one or more DC applied signals, each applied signal being in the form of a selected applied signal form, one or more applied signal applicators for administering the applied signals to test zones on the skin of a human subject, and one or more applied signal resistance sensors for sensing the resistance of the skin of the subject at the test zones.

U.S. Pat. No. 8,332,027 for electroacupuncture system and method for determining meridian energy balance number by inventor Larsen, filed May 12, 2010 and issued Dec. 11, 2012, is directed to an electroacupuncture system for measuring and treating meridian energy balance in a patient. The system also includes a processing apparatus connected to the electrical potential source capable of calculating an overall meridian energy balance number. The processing apparatus may be programmed to carry out a method for determining a meridian energy balance number.

U.S. Pat. No. 8,682,425 for electropuncture system by inventors Larsen, et al., filed Jan. 30, 2008 and issued Mar. 25, 2014, is directed to an electroacupuncture system for measuring and treating meridian energy balance in a patient. The system can include a pressure sensitive probe and return path contact, both of which are connected to an electrical potential source. The probe and contact are meant to be applied to a patient to diagnose and treat meridian energy imbalances. The system also includes a processing apparatus connected to the electrical potential source capable of interpreting the readings taken by the electrical potential source and probe and affecting operation of the system based on the readings. The processing apparatus may also use measurements to calculate an overall meridian energy balance number.

U.S. Publication No. 20150230726 for comprehensive health assessment tool for identifying acquired errors of metabolism by inventor Greaves, filed May 14, 2014 and published Aug. 20, 2015, is directed to a method of comprehensive health assessment includes using a biocommunication or bioenergetic device to measure signals sent across or through the body. Fluctuations in galvanic skin response are measured and transmitted to a computer or computing device and compared to a library of possible stimulus sources, each associated with a predetermined electrical signature.

U.S. Publication No. 20180042813 for smart equipment with bidirectional diagnosis and therapy device by inventor Chiang, filed Aug. 15, 2015 and published Feb. 15, 2018, is directed to a smart equipment with bidirectional diagnosis and therapy device, comprising a power supply unit used for providing each unit with required power, a high-voltage diagnosis and therapy unit provided for diagnosis and therapy as well as electronic acupuncture and sending back a diagnosis and therapy signal, an input and display unit provided for inputting operation commands and displaying related image, a wireless transmission unit provided for connecting to a cloud database wirelessly, a magnetic disk installed with program being loaded with application software for processing the diagnosis and therapy signal correspondingly, and a microprocessor used for processing related operation. Thereby, the present invention enables the user to manipulate the high-voltage diagnosis and therapy unit for diagnosis and therapy via the input and display unit according to suggestion from application software. Thus, correct diagnosis and therapy is allowed for the user to achieve the best effect.

SUMMARY OF THE INVENTION

The present invention relates to devices, methods, and systems for measuring galvanic skin response based on exposure to stimuli including electromagnetic waves and mechanical waves as well as substances exposed to electromagnetic waves and mechanical waves.

It is an object of this invention to provide intelligent analytics and actionable data based on galvanic skin response measurements obtained during exposure to stimuli including electromagnetic waves and mechanical waves and substances exposed to electromagnetic waves and mechanical waves.

In one embodiment, the present invention is directed to a system for measuring galvanic skin response, including an electrical conductivity meter electrically connected to a positive electrode and a negative electrode; and a server platform in network communication with the electrical conductivity meter; wherein the electrical conductivity meter includes at least one processor and at least one memory; wherein the negative electrode is in contact with a first portion of a subject and wherein the positive electrode is in contact with a second portion of a subject, thereby creating a circuit including the positive electrode, the negative electrode, and the subject; wherein the positive electrode includes a pressure sensor operable to indicate an amount of pressure applied by a tip of the positive electrode on the point; wherein the server platform includes a reasoning engine; and wherein the reasoning engine is operable to detect variations in the pressure applied by the positive electrode.

In another embodiment, the present invention is directed to a system for measuring galvanic skin response, including an electrical conductivity meter electrically connected to a positive electrode and a negative electrode; and a server platform in network communication with the electrical conductivity meter; wherein the electrical conductivity meter includes at least one processor, at least one memory, a display screen, and a test plate operable to receive at least one element exposed to electromagnetic waves and/or mechanical waves; wherein the negative electrode is in contact with a first portion of a subject and wherein the positive electrode is in contact with a second portion of a subject, thereby creating a circuit including the positive electrode, the negative electrode, and the subject; wherein the circuit further includes the at least one element exposed to the electromagnetic waves and/or the mechanical waves in contact with the test plate; and wherein the server platform is operable to calculate a compatibility score for the at least one element exposed to the electromagnetic waves and/or the mechanical waves and the subject based on a galvanic skin measurement of the subject when the at least one element exposed to the electromagnetic waves and/or the mechanical waves is in contact with the test plate and thereby included in the circuit and a galvanic skin measurement of the subject when the at least one element exposed to the electromagnetic waves and/or the mechanical waves is not in contact with the test plate and thereby not included in the circuit, wherein the compatibility score indicates a degree of effectiveness, a degree of sensitivity, a degree of tolerance, and/or a tendency to toxicity of the at least one element exposed to the electromagnetic waves and/or the mechanical waves for the subject.

In yet another embodiment, the present invention is directed to a system for measuring galvanic skin response, including an electrical conductivity meter electrically connected to a positive electrode and a negative electrode; a server platform in network communication with the electrical conductivity meter; and a device including a photon source and/or a Tesla coil operable to emit electromagnetic waves; wherein the electrical conductivity meter includes at least one processor, at least one memory, a display screen, and a test plate operable to receive at least one element exposed to electromagnetic waves and/or mechanical waves; wherein the negative electrode is in contact with a first portion of a subject and wherein the positive electrode is in contact with a second portion of a subject, thereby creating a circuit including the positive electrode, the negative electrode, and the subject; wherein the circuit further includes the at least one element exposed to the electromagnetic waves and/or the mechanical waves in contact with the test plate; wherein the server platform is operable to calculate a compatibility score for the at least one element exposed to the electromagnetic waves and/or the mechanical waves and the subject based on a galvanic skin measurement of the subject when the at least one element exposed to the electromagnetic waves and/or the mechanical waves is in contact with the test plate and a galvanic skin measurement of the subject when the at least one element exposed to the electromagnetic waves and/or the mechanical waves is not in contact with the test plate, wherein the compatibility score indicates a degree of effectiveness, a degree of sensitivity, a degree of tolerance, and/or a tendency to toxicity of the at least one element exposed to the electromagnetic waves and/or the mechanical waves for the subject; wherein the device including the photon source and/or the Tesla coil is configured to expose the at least one element to the electromagnetic waves; and wherein the at least one element includes food, a food component, a coloring, an additive, a preservative, a thickener, a stabilizer, an emulsifier, an enhancer, a beverage, a supplement, a medication, a drug, an herb, a spice, a vitamin, a mineral, a gemstone, a metal, an electronic device, a bodily fluid, a tissue, and/or a hair sample.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 6A illustrates a first side of a band electrode according to one embodiment of the present invention.

FIG. 6B illustrates a second side of the band electrode in FIG. 6A.

FIG. 6C illustrates a patch electrode according to one embodiment of the present invention.

DETAILED DESCRIPTION

Figure 1:
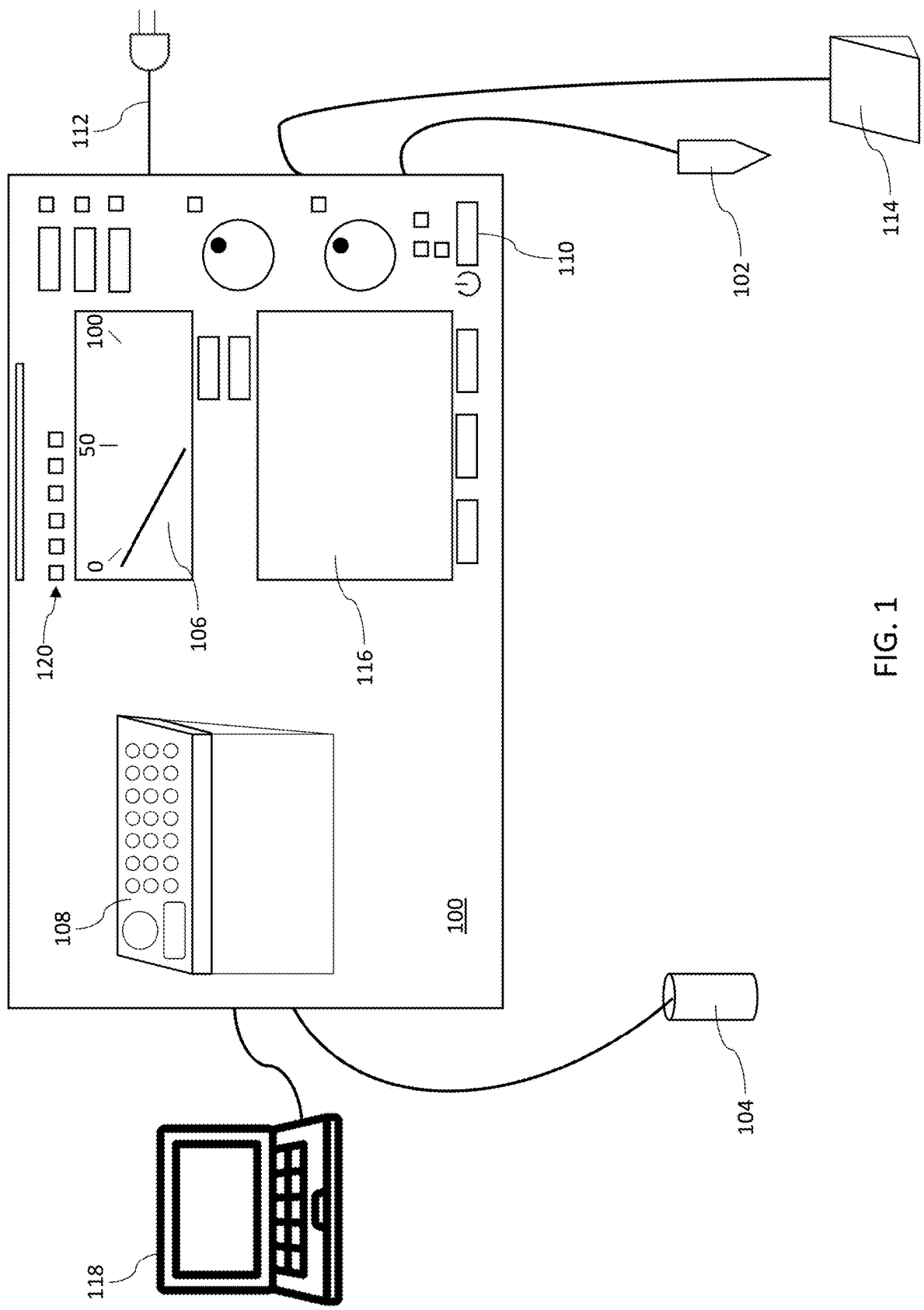
FIG. 1 illustrates one embodiment of an EAV device.

The present invention is generally directed to galvanic skin response measurements and analytics.

In one embodiment, the present invention is directed to a system for measuring galvanic skin response, including an electrical conductivity meter electrically connected to a positive electrode and a negative electrode; and a server platform in network communication with the electrical conductivity meter; wherein the electrical conductivity meter includes at least one processor and at least one memory; wherein the negative electrode is in contact with a first portion of a subject and wherein the positive electrode is in contact with a second portion of a subject, thereby creating a circuit including the positive electrode, the negative electrode, and the subject; wherein the positive electrode includes a pressure sensor operable to indicate an amount of pressure applied by a tip of the positive electrode on the point; wherein the server platform includes a reasoning engine; and wherein the reasoning engine is operable to detect variations in the pressure applied by the positive electrode.

In another embodiment, the present invention is directed to a system for measuring galvanic skin response, including an electrical conductivity meter electrically connected to a positive electrode and a negative electrode; and a server platform in network communication with the electrical conductivity meter; wherein the electrical conductivity meter includes at least one processor, at least one memory, a display screen, and a test plate operable to receive at least one element exposed to electromagnetic waves and/or mechanical waves; wherein the negative electrode is in contact with a first portion of a subject and wherein the positive electrode is in contact with a second portion of a subject, thereby creating a circuit including the positive electrode, the negative electrode, and the subject; wherein the circuit further includes the at least one element exposed to the electromagnetic waves and/or the mechanical waves in contact with the test plate; and wherein the server platform is operable to calculate a compatibility score for the at least one element exposed to the electromagnetic waves and/or the mechanical waves and the subject based on a galvanic skin measurement of the subject when the at least one element exposed to the electromagnetic waves and/or the mechanical waves is in contact with the test plate and thereby included in the circuit and a galvanic skin measurement of the subject when the at least one element exposed to the electromagnetic waves and/or the mechanical waves is not in contact with the test plate and thereby not included in the circuit, wherein the compatibility score indicates a degree of effectiveness, a degree of sensitivity, a degree of tolerance, and/or a tendency to toxicity of the at least one element exposed to the electromagnetic waves and/or the mechanical waves for the subject.

In yet another embodiment, the present invention is directed to a system for measuring galvanic skin response, including an electrical conductivity meter electrically connected to a positive electrode and a negative electrode; a server platform in network communication with the electrical conductivity meter; and a device including a photon source and/or a Tesla coil operable to emit electromagnetic waves; wherein the electrical conductivity meter includes at least one processor, at least one memory, a display screen, and a test plate operable to receive at least one element exposed to electromagnetic waves and/or mechanical waves; wherein the negative electrode is in contact with a first portion of a subject and wherein the positive electrode is in contact with a second portion of a subject, thereby creating a circuit including the positive electrode, the negative electrode, and the subject; wherein the circuit further includes the at least one element exposed to the electromagnetic waves and/or the mechanical waves in contact with the test plate; wherein the server platform is operable to calculate a compatibility score for the at least one element exposed to the electromagnetic waves and/or the mechanical waves and the subject based on a galvanic skin measurement of the subject when the at least one element exposed to the electromagnetic waves and/or the mechanical waves is in contact with the test plate and a galvanic skin measurement of the subject when the at least one element exposed to the electromagnetic waves and/or the mechanical waves is not in contact with the test plate, wherein the compatibility score indicates a degree of effectiveness, a degree of sensitivity, a degree of tolerance, and/or a tendency to toxicity of the at least one element exposed to the electromagnetic waves and/or the mechanical waves for the subject; wherein the device including the photon source and/or the Tesla coil is configured to expose the at least one element to the electromagnetic waves; and wherein the at least one element includes food, a food component, a coloring, an additive, a preservative, a thickener, a stabilizer, an emulsifier, an enhancer, a beverage, a supplement, a medication, a drug, an herb, a spice, a vitamin, a mineral, a gemstone, a metal, an electronic device, a bodily fluid, a tissue, and/or a hair sample.

Referring now to the drawings in general, the illustrations are for the purpose of describing one or more preferred embodiments of the invention and are not intended to limit the invention thereto.

Electromagnetic waves and mechanical waves are two prominent methods of energy transfer. Generally, electromagnetic waves are emitted by accelerating electrically charged particles. When an electromagnetic wave contacts matter, the electromagnetic wave exerts force on that matter, and is capable of imparting energy, momentum, and angular momentum to that matter. Examples of electromagnetic waves include radio waves, microwaves, infrared, visible light, ultraviolet (UV) light, X-rays, and gamma rays. In contrast, mechanical waves are an oscillation of matter which transfers energy through a medium. Examples of mechanical waves include sound waves, seismic waves, and ocean waves.

Accordingly, both electromagnetic and mechanical waves are capable of transforming the structure of a substance. The structure of liquids such as water is transformed in nature through light from the sun, natural electrical discharges such as lightning, and other natural processes. It is also possible to produce structured or hexagonal water, as well as to change the structure of water through purification as described in U.S. Pat. No. 7,793,788 titled "Separating components of aqueous mixtures, suspensions, and solutions", which is incorporated herein by reference in its entirety. Similarly, magnetic fields, electric fields, and electromagnetic fields are capable of transforming the structure of a substance.

Several methods of exposing substances to mechanical waves and electromagnetic waves are known in the art. QUINT DRINK by QUINTSYSTEME exposes a liquid such as water to vibrations, thereby transferring energy to the liquid and altering the structure of the liquid. Similarly, the ULTRACOMPAKT BIOENERGETISCHER STIMULATOR (UBS) 315 by Dieter Jossner utilizes microelectronics, LEDs, and a magnetic field to transfer energy to substances and alter the structure of the substances. Specifically, the UBS 315 is capable of producing photons in the form of white light and red light, which is modulated with solar noise. Additionally, the UBS 315 includes an audio socket which provides for modulating the photons and the magnetic field with audio. The magnetic field of the UBS 315 is a scalar magnetic field produced by a Tesla coil. Advantageously, the UBS 315 is operable to alter the structure of both liquids and solids. Similarly, Dieter Jossner's AQA 707 provides for treating water and other liquids with light including the frequency spectrum of the sun, magnetic fields, energetic fields, and through a vortex effect.

Recent research has also shown that exposure to biometric sounds is beneficial. For example, a paper titled "Mother's voice and heartbeat sounds elicit auditory plasticity in the human brain before full gestation" by Alexandra R. Webb, Howard T. Heller, Carol B. Benson, and Amir Lahav (published in Proceedings of the National Academy of Sciences of the United States of America on Mar. 10, 2015) demonstrated that newborns who were exposed to audio recordings of maternal sounds including their mother's voice and their mother's heartbeat developed a significantly larger auditory cortex compared to newborns who were not exposed to such auditory recordings. Similarly, Stanford University has been granted U.S. Pat. No. 9,888,884 titled "Method of sonifying signals obtained from a living subject", which describes providing aural signals based on a subject's heart or brain to the subject as biofeedback. The biofeedback includes neurotherapy, which is utilized as a therapy for migraines, autism, attention deficit hyperactivity disorder (ADHD), and/or cognitive performance.

What is needed are systems and methods for quantitatively measuring a subject's reaction to electromagnetic and mechanical waves and compatibility with electromagnetic and mechanical waves, as well as a subject's reaction to and compatibility with substances exposed to electromagnetic and mechanical waves. In particular, none of the prior art discloses quantitatively measuring a subject's reaction to light and/or sound constructed based on measurable biological outputs or substances exposed to light and/or sound constructed based on measurable biological outputs.

One embodiment of the present invention includes measuring, recording, or otherwise obtaining biological outputs and/or biometric sounds from a subject or a living being of interest. Biological outputs include, by way of example and not limitation, heartbeats, brainwaves, neural oscillations, breathing patterns, and/or combinations thereof. Alternatively, resonance frequencies of a subject or a living being of interest including resonance frequencies of organs, bones, tissue, and/or cartilage. By way of example the resonance frequencies of a spinal column, a head, a chest wall, an abdomen, shoulders, lungs, legs, arms, hands, feet, an ocular globe, and/or a maxilla are measured and recorded as vibrations and/or sound waves. In another embodiment, resonance frequencies of an object, or natural occurrences such as lightning, the ionosphere of a planet, etc. are measured and recorded as vibrations and/or sound waves. Biometric sounds include speech (e.g., mother's voice). The biological outputs' resonance frequencies, or biometric sounds are recorded using a digital recorder or an analog recorder. Alternatively, the biological outputs, resonance frequencies, or biometric sounds are measured by a particular machine such as an electroencephalography (EEG) machine, an electrocardiography (ECG) machine, or a machine that measures resonance frequencies such as the 353B34 PCB accelerometer by PCB PIEZOTRONICS or the ULTRALIGN G2 by SIGMA INSTRUMENTS.

The living being of interest includes a living being known to the subject or related to the subject, by way of example and not limitation, a subject, a member of a subject's family such as a spouse, father, mother, child, grandchild, brother, sister, cousin, aunt, uncle, grandfather, grandmother, etc., a significant other, a friend, or a pet such as a dog or a cat. Alternatively, the living being of interest includes a living being not personally known to the subject, such as an athlete, celebrity, or a living being with certain qualities such as physical qualities, emotional qualities, spiritual qualities, mental qualities, etc. Alternatively, the living being of interest includes an animal, a mammal, a reptile, amphibian, fish, bird, bacteria, virus, plant, etc. In one embodiment of the present invention, the term animal includes a human. In another embodiment of the present invention, the term animal does not include a human. In another embodiment, the living being of interest was previously living and is now deceased.

Resonance frequencies of objects in one embodiment include resonance frequencies of objects with significance to a living being of interest, such as an object from childhood, an object of a family member or friend, an object associated with a professional or personal achievement, etc.

In one embodiment, the resonance frequencies and/or biological outputs are recorded as a mechanical wave such as a sound or a vibration. The recording is preferably digital, but is an analog recording in another embodiment. Sounds are recorded via any method known to one skilled in the art, such as via a microphone connected to a recorder operable to record to a magnetic tape device or a microphone connected to an electronic device such as a laptop, tablet, smart phone, etc. running an application program. Vibrations are recorded utilizing a vibration data logger, a vibration meter, and/or any other apparatus known in the art for recording vibrations. Once recorded, the sounds and/or vibrations are operable to be combined to produce a combined sound or vibration.

In another embodiment, a sound and/or vibration is converted or translated into electromagnetic waves such as visible light. SOUND OF SOUL by AQUAQUINTA (Austria) provides for translation of heart rate variability (HRV) into sound and/or colored light. Additionally, US Pub. No. 2017/0007847 titled "Bioresonance frequency emitting device, system, and method" which is incorporated herein by reference in its entirety, provides one or more LEDs which emit light at a certain intensity, frequency, or flicker-rate based on one or more bioresonances. The present invention provides for translation of any mechanical wave and/or electromagnetic wave or groups of mechanical waves and/or electromagnetic waves into another mechanical wave and/or electromagnetic wave and/or groups of other mechanical waves and/or electromagnetic waves. In one example, music is converted into light or a sound vibration. In another example, a sound and/or vibration is converted or translated into an audio file such as a musical track, a binaural beat track, a track of a natural sound such as ocean waves or wildlife, or a track of someone speaking. U.S. Pat. No. 9,888,884, which is incorporated herein by reference in its entirety, describes determining the beats per minute (BPM) of biometric data and translating the BPM into rhythmic content such as music. Similarly, the BPM of the sound and/or vibration is operable to be converted into rhythmic content in the present application. Alternatively, the BPM of the sound and/or vibration is operable to be matched against a database of music for matches to the sound and/or vibration. Music and musical tracks include tonal and atonal music and music from any genre such as electronic, rock, soul, R&B, hip-hop, reggae, folk, country, classical, jazz, avant-garde, and all sub-genres thereof.

In another embodiment, the present invention provides for a device or system exposing a substance to electromagnetic and/or mechanical waves. Exposure to the electromagnetic and/or mechanical waves alters the structure of the substance. In one embodiment, this exposure is performed with the ULTRACOMPAKT BIOENERGETISCHER STIMULATOR (UBS) 315 or another device with photon sources and/or a Tesla coil. The photon source of the device preferably emits red and white photons. Additionally, the Tesla coil preferably has a 40% scalar content with an approximate field strength of 150 µT. Alternatively, a device is operable to create magnetic, electric, and/or electromagnetic fields through a combination of magnets, electromagnets, and/or coils.

In another alternative, a substance is exposed to mechanical waves such as the waves in an ocean or a lake. The substance is exposed directly in one embodiment, but alternatively is placed in a container and exposed to the waves.

The present invention also provides for exposing a substance to one or more volatile chemical compounds or odors which alter the structure of the substance. Alternatively, the volatile chemical compounds or odors are translated into a digital signal. One method of translating the volatile chemical compounds or odors into digital signals is described in WIPO Pub. No. WO2019040910A1, which is incorporated herein by reference in its entirety.

The substance exposed includes any liquid, solid, and/or gas. Examples of common substances include a food, a food component (e.g., coloring, additive, preservative, thickener, stabilizer, emulsifier, enhancer), a beverage, a supplement, a medication, a drug, an herb, a spice, a vitamin, a mineral, a gemstone, a metal, an electronic device, a bodily fluid, a tissue, and/or a hair sample.

As previously discussed, Dr. Reinhard Voll, a German physician and engineer, developed a method of measuring galvanic skin response known as Electroacupuncture According to Voll (EAV) in the 1940s. EAV is one application of measuring galvanic skin response. EAV utilizes principles of acupuncture based on meridians. EAV differs from traditional Chinese acupuncture in that there are 21 basic EAV meridians instead of 12 principal meridians. Acupuncture points on these meridians correspond to glands, internal organs, and/or subcomponents of internal organs. Electrical conductivity of the skin is higher on acupuncture points than on other locations. Dr. Helmut Schimmel improved EAV in the 1970s by utilizing a single acupuncture point instead of multiple points.

An electrical conductivity meter is used to measure galvanic skin response. An EAV device is one type of electrical conductivity meter. A practitioner tests a meridian point with a probe that corresponds to a positive electrode. The positive electrode is preferably a stylus with a brass or silver tip. A subject contacts (e.g., holds) a negative electrode. The practitioner tests the conductivity of a plurality of meridian points by contacting the skin of the subject with the positive electrode at a specific meridian point on the hands or feet. The negative electrode and positive electrode are electrically connected to the EAV device (e.g., via cables). A small amount of current travels through the body when the positive electrode contacts the skin.

FIG. 1 illustrates one embodiment of an EAV device. The EAV device 100 is electrically connected to a probe 102 (i.e., positive electrode) and a negative electrode 104. A meter 106 displays a conductivity reading between 0 and 100. A test plate 108 is used to test at least one element. A power button 110 is used to turn the EAV device 100 on or off. A power cord 112 connects the EAV device 100 to alternating current (AC) power. Alternatively, the EAV device is powered by at least one battery (e.g., rechargeable battery). A foot pedal 114 is optionally used to toggle between menu items displayed on a screen 116. In one embodiment, the screen is a touch screen. The EAV device 100 is connected via a wired connection or a wireless connection to a computing device 118. The EAV device 100 preferably has a pressure range indicator 120 to indicate a pressure exerted by the tip of the probe 102 on a surface (e.g., skin). Manuals for the Vega® BIO-expert and the Wegamed™ Test Expert Plus include additional details regarding EAV devices, each of which is incorporated herein by reference in its entirety. Additional information regarding testing is included in the "Short Manual of the VEGATEST-method" by Fehrenbach et al., including both the $2^{nd}$ ed. (1986) and SKU no. FLIT0.13059, available at https://www.wegamed.de/product/short-manual-of-the-vegatest-method-2/, each of which is incorporated herein by reference in its entirety.

The probe preferably includes a pressure sensor to indicate an amount of pressure exerted by the tip of the probe on a surface. In another embodiment, the probe includes a three-dimensional (3D) accelerometer to measure a position (e.g., angle) of the probe. Alternatively or additionally, the probe includes a 3D gyroscope to measure a position or angle of the probe.

The EAV device preferably includes at least one processor. By way of example, and not limitation, the at least one processor is a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof operable to perform calculations, process instructions for execution, and/or otherwise manipulate information. In one embodiment, one or more of the at least one processor is operable to run predefined programs stored in at least one memory of the EAV device.

The EAV device preferably includes at least one antenna, which allows the EAV device to transmit data to at least one computing device (e.g., smartphone, tablet, laptop computer, desktop computer). In a preferred embodiment, the EAV device is in wireless network communication with the at least one computing device. The wireless communication is, by way of example and not limitation, radio frequency (RF), BLUETOOTH, ZIGBEE, WI-FI, wireless local area networking, near field communication (NFC), or other similar commercially utilized standards. Alternatively, the at least one computing device is in wired communication with the control unit through universal serial bus (USB), FireWire®, or equivalent.

Figure 2:
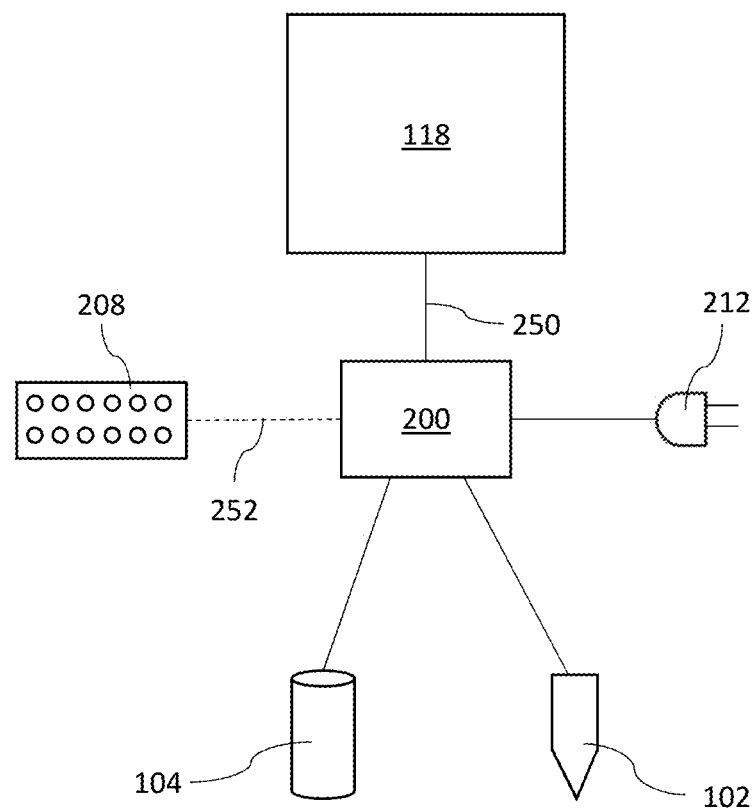
FIG. 2 illustrates another embodiment of an EAV device.

FIG. 2 illustrates another embodiment of an EAV device. In this embodiment, the EAV device 200 is connected via a wired connection (e.g., cable 250) to the computing device 118 (e.g., smartphone, tablet, laptop computer, desktop computer). A power cord 212 connects the EAV device 200 to alternating current (AC) power. Alternatively, the EAV device is powered by at least one battery (e.g., rechargeable battery). The EAV device 200 is connected to the probe 102 and the negative electrode 104. A test plate 208 is selectively added or removed to the EAV device 200 via a test plate cable 252. Advantageously, the EAV device 200 provides for greater portability than the EAV device shown in FIG. 1 due to its modular nature and use of at least one processor on the computing device.

Figure 3A:
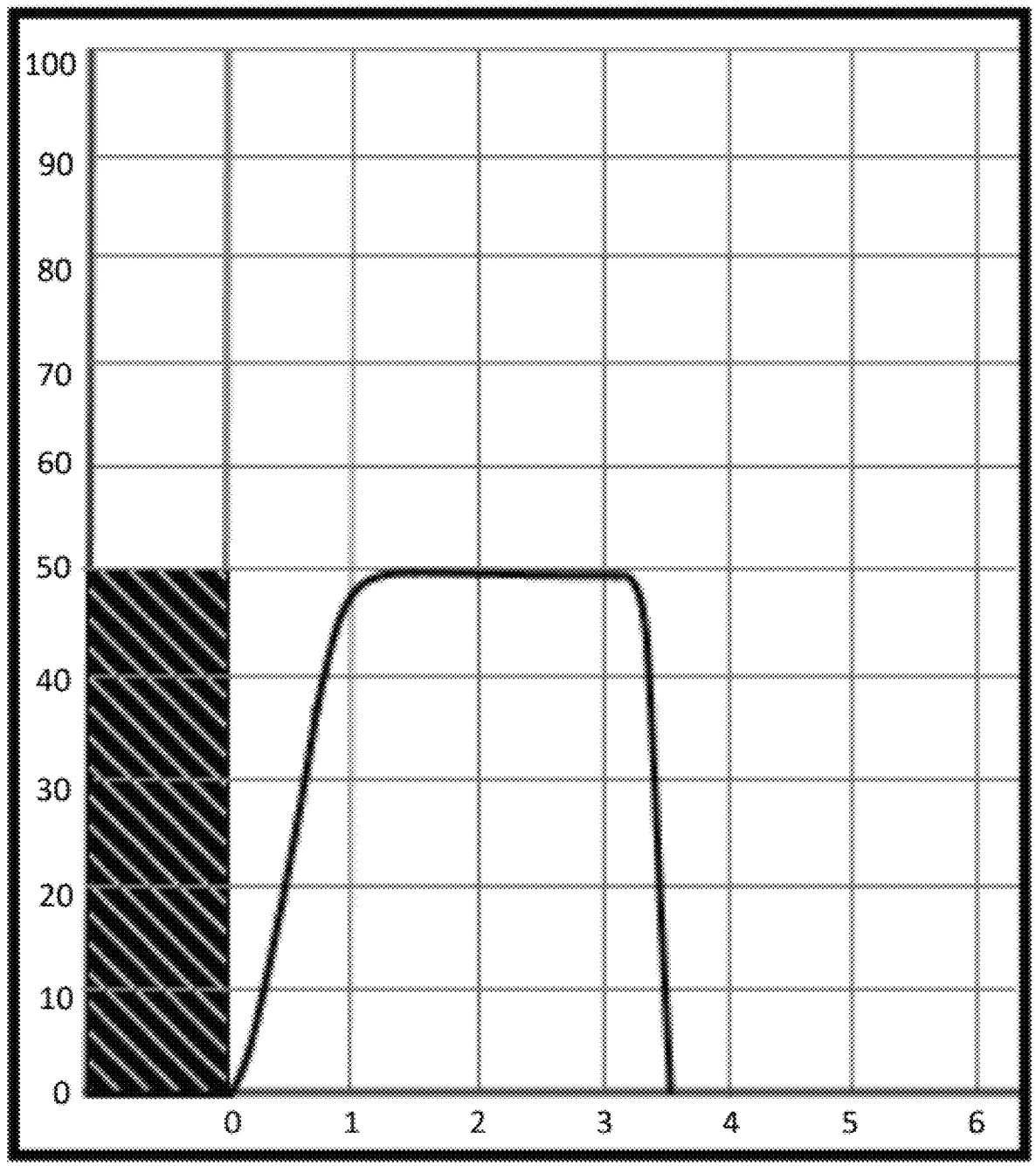
FIG. 3A illustrates a conductivity reading of a balanced meridian.
Figure 3B:
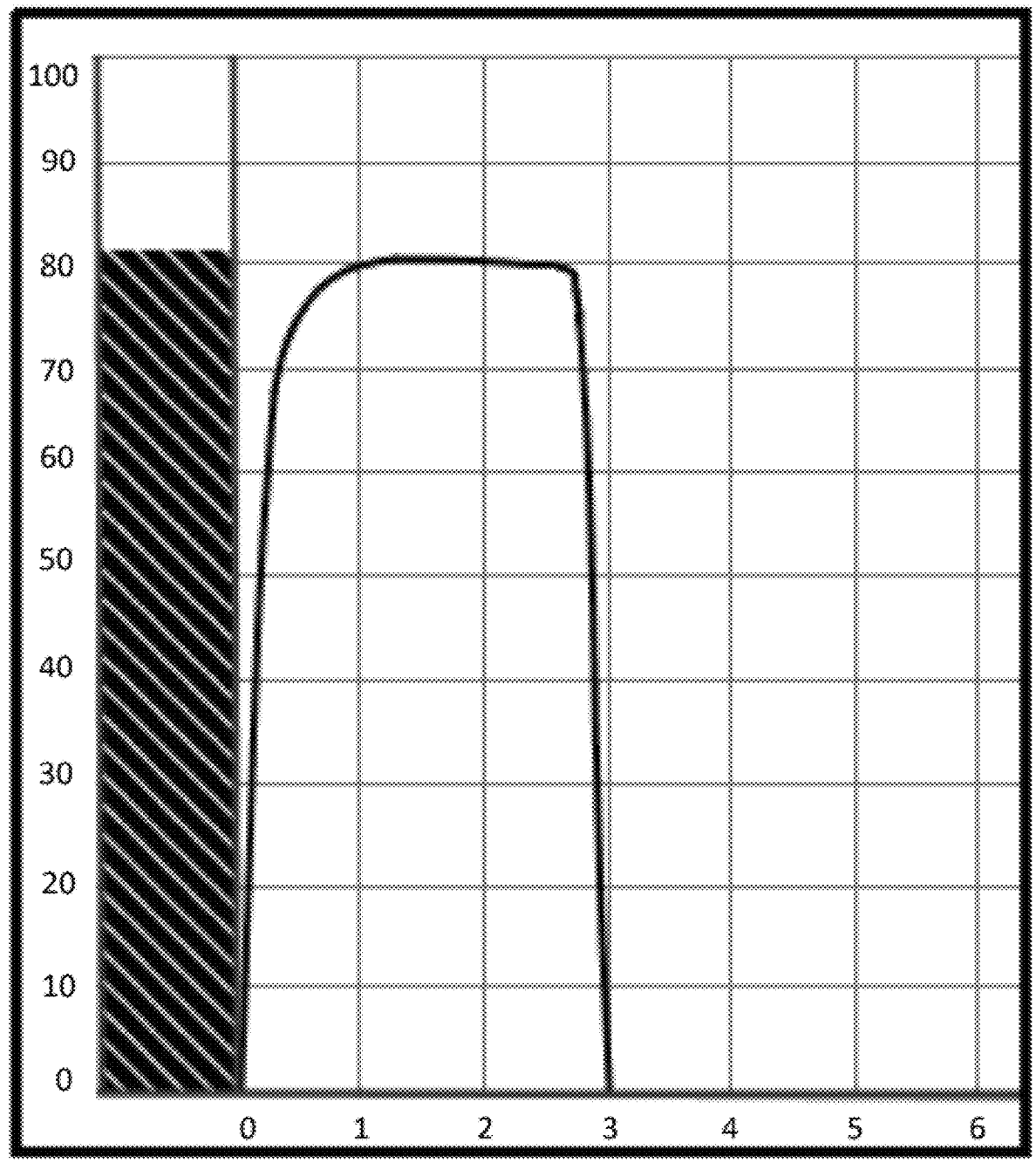
FIG. 3B illustrates a conductivity reading of an irritated or inflamed meridian.
Figure 3C:
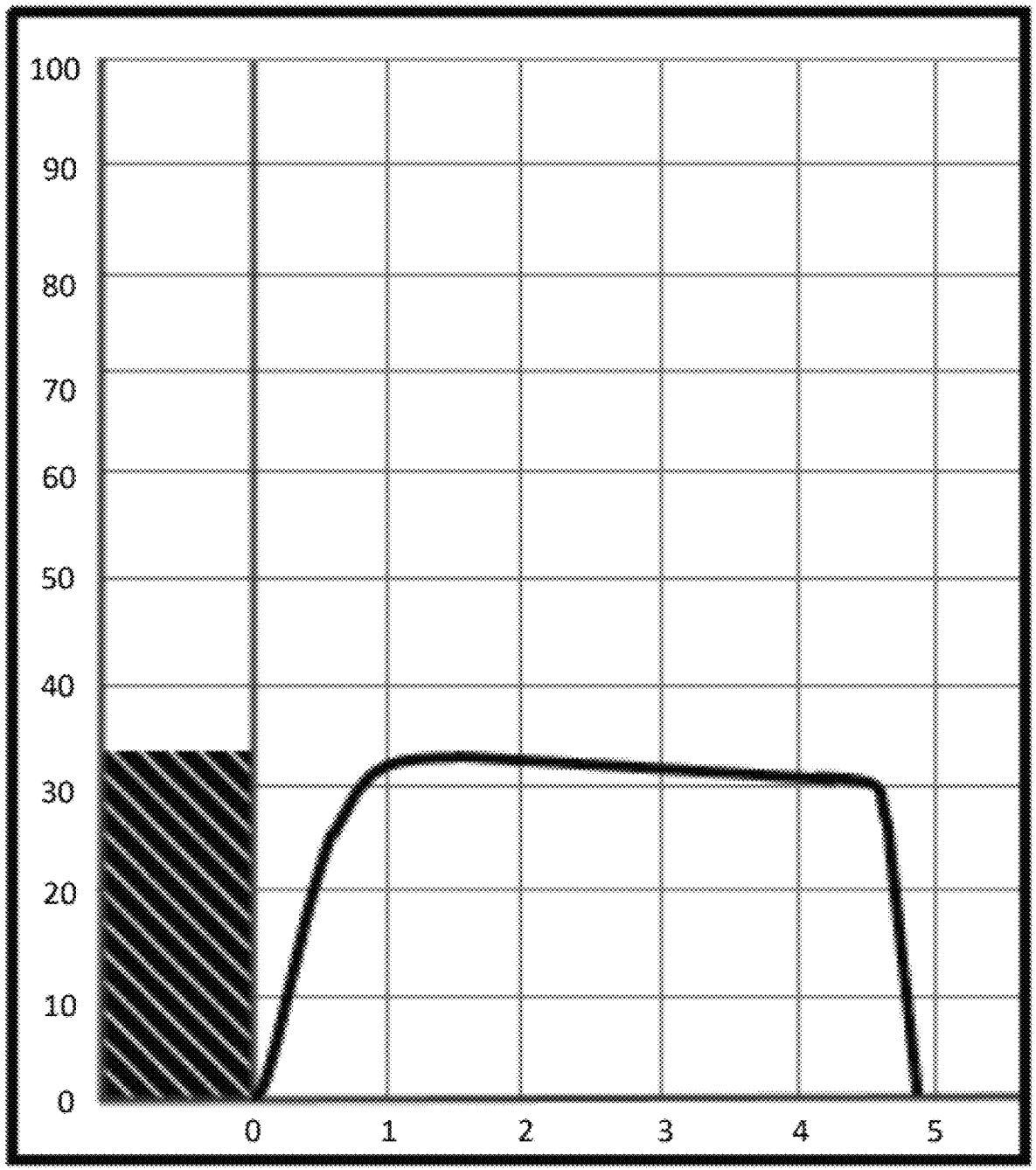
FIG. 3C illustrates a degenerated or impaired meridian.

An EAV device uses a voltage of less than 1.5V and a measurement current of less than 12 µA. In a preferred embodiment, the EAV device uses a voltage of 1.5V and a measurement current of 10 µA. The EAV device is calibrated to give a conductivity reading of 0 to 100. A balanced meridian has a conductivity reading of 50 or approximately 50 as shown in FIG. 3A. A conductivity reading greater than 50 or greater than approximately 50 (e.g., >55) indicates irritation or inflammation of the meridian as shown in FIG. 3B. Inflamed tissue swells with water, which results in a higher electrical conductivity. A conductivity reading less than 50 or less than approximately 50 (e.g., <45) indicates degeneration or impairment of the meridian as shown in FIG. 3C. A chronically impaired organ becomes harder and loses hydration, which results in a lower electrical conductivity.

Figure 4:
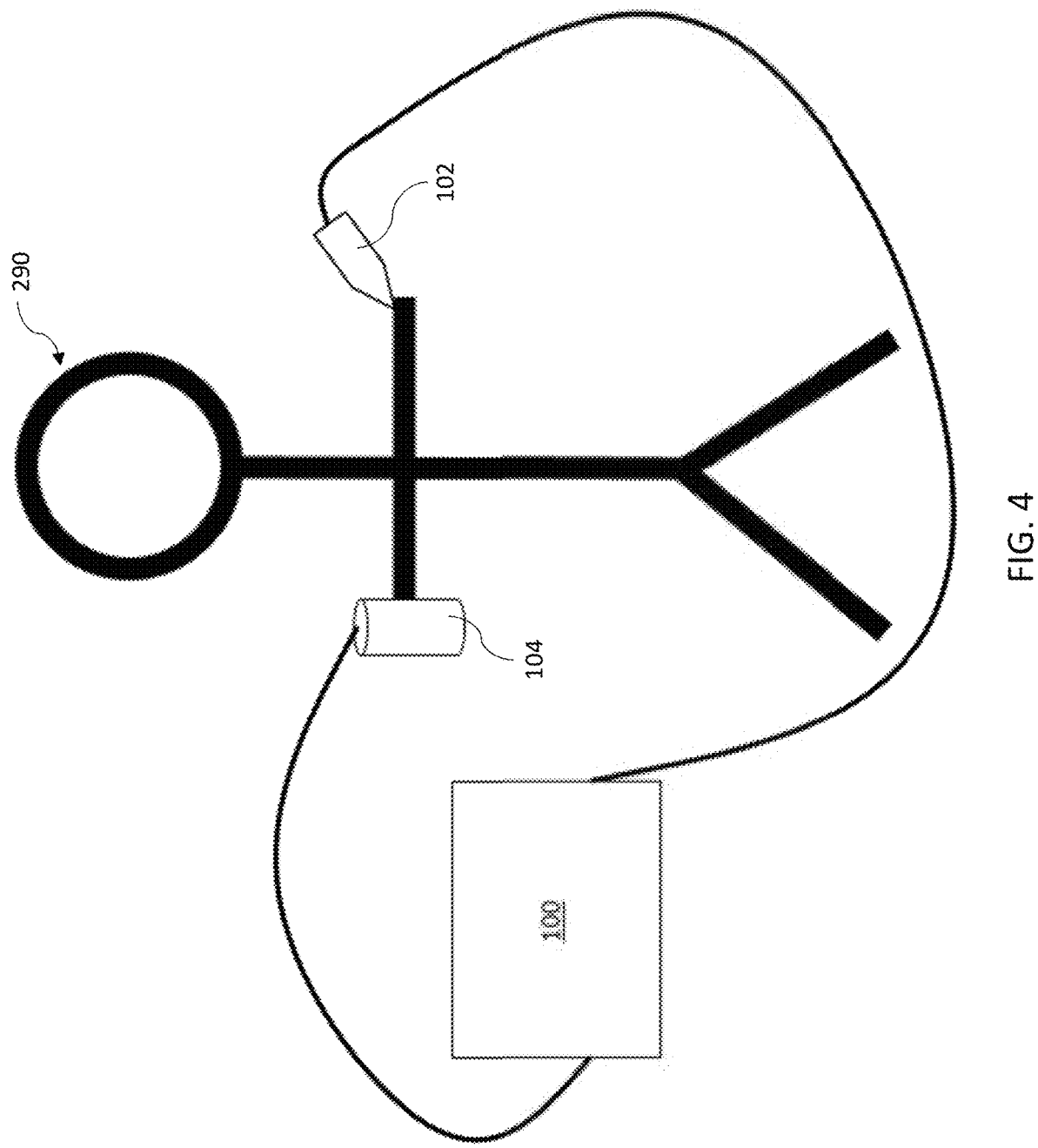
FIG. 4 illustrates a circuit created between a subject and an EAV device according to one embodiment of the present invention.

FIG. 4 illustrates a circuit created between a subject and an EAV device. As previously described, the EAV device 100 is connected to a probe 102 (i.e., positive electrode) and a negative electrode 104. The probe 102 is shown contacting a subject 290 on a first hand. A second hand of the subject 290 is holding the negative electrode 104. Touching the probe 102 to the first hand while the subject 290 holds the negative electrode 104 creates a circuit. In another embodiment, the circuit also includes at least one element (e.g., food, beverage, supplement) on the test plate of the EAV device.

Figure 5:
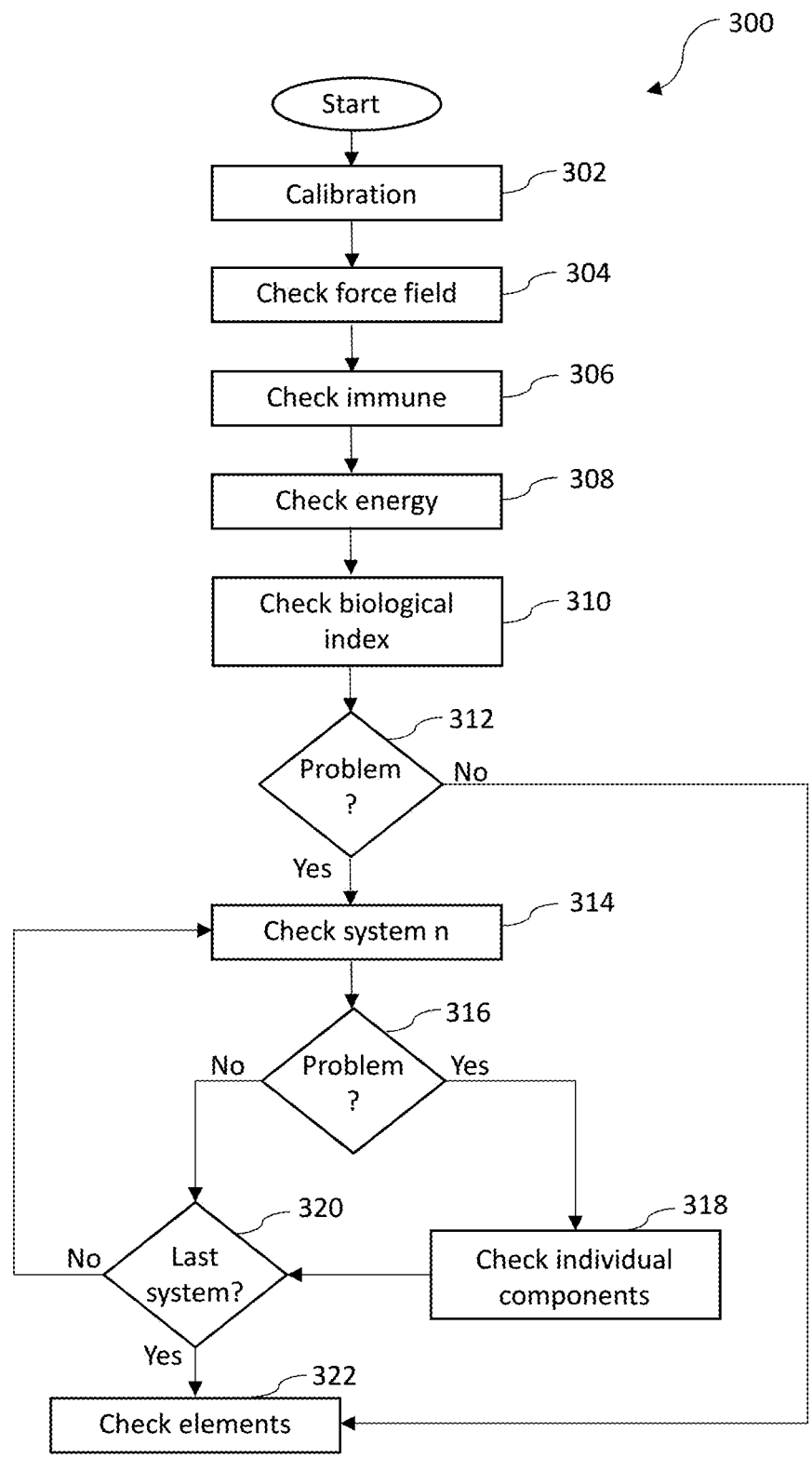
FIG. 5 is a flow chart detailing a method of calibrating and testing using the EAV device according to one embodiment of the present invention.

FIG. 5 is a flow chart detailing a method of calibrating and testing using the EAV device. The method 300 includes a step of calibrating 302 the EAV device. The calibration includes setting a noise threshold and determining whether signals need to be amplified. After calibration, the method 300 includes a step 304 of checking a force field of the subject, a step 306 of checking an immune system of the subject, and a step 308 of checking an energy level of the subject. Steps 304-308 create a baseline for the reading.

A biological index of the subject is measured in step 310. The biological index is preferably a characteristic of the mesenchyme (i.e., connective tissue). The connective tissue reflects a biological age of a subject. In a preferred embodiment, the biological index includes numbers between 1 and 21, wherein lower numbers (e.g., 1) correspond to younger biological age and higher numbers (e.g., 21) correspond to higher biological age. In another embodiment, a biological index value of 15 or greater reflects a health problem.

In step 312, it is determined whether there is a problem with the biological index of the subject (e.g., value >15). If there is not a problem with the biological index, the method 300 proceeds to step 322. If there is a problem with the biological index, a biological subsystem of a plurality of biological subsystems is checked in step 314. After the measurement of the biological subsystem, it is determined whether there is a problem with the biological subsystem (e.g., conductivity reading >55, conductivity reading <45) in step 316. If there is a problem with the biological subsystem, individual components within the biological subsystem are checked for problems in step 318. The problems include, but are not limited to, increased acidity, presence of at least one bacterium, presence of at least one virus, and imbalance of yeast. After all individual components within the biological subsystem are checked for problems, it is determined in step 320 whether the biological subsystem tested in step 314 was the final biological subsystem. If there was not a problem with the biological subsystem in step 316, the method 300 proceeds to step 320. If the biological subsystem was not the final biological subsystem, the method 300 returns to step 314. If the biological subsystem was the final biological system, at least one element is tested in step 322.

To test reactions to different elements, at least one element is placed in and/or on a test plate to put the at least one element in circuit with the subject. The test plate is preferably formed of metal. In a preferred embodiment, the test plate includes a plurality of cylindrical holes drilled into the test plate. Each of the plurality of cylindrical holes is operable to hold an ampule or a vial of an element to be tested.

The at least one element includes, but is not limited to, a food, a food component (e.g., coloring, additive, preservative, thickener, stabilizer, emulsifier, enhancer), a beverage, a supplement, a medication, a drug, an herb, a spice, a vitamin, a mineral, a gemstone, a metal, an electronic device, a bodily fluid, a tissue, and/or a hair sample. The test plate allows for one or more of the at least one element to be selectively added or selectively removed from the circuit.

In a preferred embodiment, the ampule or the vial containing the at least one element is labeled to identify its contents. In one embodiment, the ampule or the vial is labeled with a barcode. Alternatively, the ampule or the vial is labeled with a passive radio frequency identification (RFID) tag. In one embodiment, a scanner for the label is connected via a cable (e.g., USB, FireWire®, or equivalent) to the EAV device. Alternatively, the scanner is built into the EAV device.

In yet another embodiment, an element library is used to store digital signatures of at least one element. An algorithm compares a conductivity reading of a subject when there is no element in the test plate with the digital signatures of the at least one element to determine whether a response to the at least one element is positive, negative, or neutral. Alternatively, a digital signature is incorporated into the testing circuit. This is accomplished in a variety of ways. In one example, a digital signature is introduced into the testing circuit by software running on the EAV device and a new conductivity measurement is obtained. Each conductivity measurement is affected by an energetic link between the subject and the digital signature. Advantageously, utilizing a digital signature allows for the at least one element to be tested without placing a sample of the at least one element on a test plate.

In another embodiment of the present invention, a conductivity reading of a subject is taken contemporaneously with exposure of the subject to electromagnetic and/or mechanical waves. The electromagnetic and/or mechanical waves include any electromagnetic and/or mechanical wave individually or in combination, including sound, vibration, light, music, etc., individually or in combination. The electromagnetic and/or mechanical waves are generated from resonance frequencies and/or biological outputs in one embodiment. Alternatively, the electromagnetic and/or mechanical waves are not generated from resonance frequencies or biological outputs but are naturally occurring electromagnetic and/or mechanical waves, machine-made electromagnetic and/or mechanical waves, or man-made electromagnetic and/or mechanical waves.

Alternatively, one or more digital signatures of electromagnetic and/or mechanical waves are created and a conductivity reading of the subject without an element in the test plate is compared with the one or more digital signatures of the electromagnetic and/or mechanical waves. In another embodiment, a digital signature is incorporated into the testing circuit.

In yet another embodiment, a substance is exposed to mechanical waves and/or electromagnetic waves and placed in the test plate and the conductivity of the subject is measured. In one embodiment, the substance is exposed to the mechanical waves and/or electromagnetic waves while in the test plate and the conductivity of the subject is measured. One or more digital signatures of substances exposed to electromagnetic and/or mechanical waves are also operable to be created and a conductivity reading of the subject without an element in the test plate is compared with the one or more digital signatures of the electromagnetic and/or mechanical waves.

The present invention also provides for measuring a conductivity reading of a subject contemporaneously with exposure of the subject to one or more volatile chemical compounds or odors. The one or more volatile chemical compounds or odors are also operable to be included in a container on the test plate in gaseous or liquid form. An example of volatile chemical compounds includes perfumes. Alternatively, volatile chemical compounds or odors collected from living beings including people, dogs, cats, etc. are collected and a conductivity reading or compatibility score determines the compatibility of the subject with the living being. Similar to the embodiments described above, the one or more volatile chemical compounds or odors are also operable to be translated into digital representations of the one or more volatile chemical compounds or odors and compared to a subject's conductivity reading or inserted into the test circuit to obtain conductivity reading(s) specific to the one or more volatile chemical compounds or odors.

In one embodiment, an EAV device is in network communication with a server platform via a computing device. The computing device is in wired or wireless communication with the EAV device. The computing device is installed with at least one application program operable to provide a graphical user interface (GUI) operable for toggling between different steps, recording testing data at different steps, and display diagnostic results and recommended treatment plans.

In one embodiment, the present invention provides a smart EAV device in direct network communication with a server platform. An example of a smart EAV device is shown in FIG. 2. The smart EAV device comprises a computing module, a communication module, and a display module. The computing module is operable to collect and process data from a testing circuit. The communication module is operable to communicate with a server platform. The display module comprises a GUI. In one embodiment, the smart EAV device is a smartphone, a tablet, a laptop, and/or any other portable device, installed with an application program in network communication with a server platform.

In one embodiment, the present invention provides a circuit toolkit including at least one signal sensor device (e.g., electrodes, bands embedded with sensors), a testing plate, and an adapter module. An example of the circuit toolkit is shown in FIG. 2. The adapter module connects the testing plate, the two electrodes, and a subject into a circuit, and transmits data signals to the EAV device.

In one embodiment, at least one electrode is configured as a patch or a band wrapping around a finger portion which includes an acupuncture point. The patch or the band includes a galvanic skin sensor to contact the acupuncture point of a subject. In one embodiment, the patch or the band is embedded with a pressure sensor to measure and display the pressure of the band on the finger to make sure the pressure is in an acceptable range. In another embodiment, the patch or the band includes a hydration sensor to measure a level of hydration of the subject. Advantageously, eliminating variability in pressure of the probe and/or the location of the probe gives more accurate results and more consistent results between practitioners. Additionally, using the patch or the band frees a practitioner's hands to run the EAV device and/or the computing device. In one embodiment, the patch or the band further includes a computing module in communication with the hydration sensor, the pressure sensor, and the galvanic skin sensor. The computing module comprises an Artificial Intelligence (AI)-based algorithm to learn the patterns of the hydration data and automatically calculates the optimal pressure for the galvanic skin sensor so as to obtain accurate testing results for a subject. Hydration data is alternatively used to normalize conductivity readings of meridians, as the hydration level of the skin affects the conductivity of skin. In another embodiment, a moisture and/or salinity sensor in the band electrode measures an amount of moisture and/or concentration of sodium in the moisture at the contact point between the band electrode and the skin and normalizes conductivity readings based on these measurements.

FIG. 6A illustrates a first side 402 of a band electrode 400 according to one embodiment of the present invention. The first side 402 includes a galvanic skin sensor (e.g., probe) 404, a hydration sensor 406, and a pressure sensor 408. The first side 402 preferably includes a computing module 410 (e.g., microprocessor) and/or an antenna 412. The computing module 410 is operable to perform calculations using data from the galvanic skin sensor 404, the hydration sensor 406, and/or the pressure sensor 408. Alternatively, data from the galvanic skin sensor 404, the hydration sensor 406, and/or the pressure sensor 408 is calculated on the EAV device and/or the server platform. The antenna 412 is operable to wirelessly transmit (e.g., via BLUETOOTH, NFC, RF, RFID, WI-FI) data to the EAV device and/or the server platform. Alternatively, data from the galvanic skin sensor 404, the hydration sensor 406, and/or the pressure sensor 408 is transmitted via a wired connection to the EAV device and/or the server platform. The first side 402 also includes hook tape 414.

FIG. 6B illustrates a second side 416 of the band electrode 400 in FIG. 6A. The second side 416 includes loop tape 418. In another embodiment, the first side includes loop tape and the second side includes hook tape. Alternatively, the band electrode is secured using an adhesive or an elastic.

FIG. 6C illustrates a patch electrode 420 according to one embodiment of the present invention. The patch electrode 420 includes a galvanic skin sensor (e.g., probe) 404, a hydration sensor 406, and a pressure sensor 408. The first side 402 preferably includes a computing module 410 (e.g., microprocessor) and/or an antenna 412. The computing module 410 is operable to perform calculations using data from the galvanic skin sensor 404, the hydration sensor 406, and/or the pressure sensor 408. Alternatively, data from the galvanic skin sensor 404, the hydration sensor 406, and/or the pressure sensor 408 is calculated on the EAV device and/or the server platform. The antenna 412 is operable to wirelessly transmit (e.g., via BLUETOOTH, NFC, RFID, WI-FI) data to the EAV device and/or the server platform. Alternatively, data from the galvanic skin sensor 404, the hydration sensor 406, and/or the pressure sensor 408 is transmitted via a wired connection to the EAV device and/or the server platform. The patch electrode 420 includes an adhesive 422 for attachment to the skin.

In one embodiment, the application program installed on the smart EAV device includes a GUI to facilitate operations, and a computing module for data collection and packaging.

In one embodiment, the smart EAV device comprises a camera operable to capture images of the testing circuit. The server platform is operable to process the captured images based on an AI/machine learning algorithm and detect any defects in the circuit and send warnings and/or suggestions to the user for correction. In one embodiment, the smart EAV device includes an AI-powered virtual assistant to verbally instruct the user for self-testing. The AI-power virtual assistant understands natural language voices, converses with the user, and executes voice commands.

In one embodiment, the server platform comprises a database storing historical data from tested subjects. The database is continuously updated with new obtained data. The historical data includes subject profile data, baseline data, diagnostic data and treatment data of tested subjects. The subject profile data includes gender, sex, age, race, and/or medical history (e.g., conditions, medications, nutritional supplements, weight, body mass index (BMI)) of a tested subject. The baseline data includes force field data, immunity data, energy level data, and volume control data for a tested subject pre-treatment and post-treatment.

In one embodiment, the server platform includes a proprietary organ library. In another embodiment, the server platform is operable to access a third-party organ library via an Application Program Interface (API).

In one embodiment, the server platform includes a proprietary problem library. The proprietary problem library includes different problem models for a specific organ. In one embodiment, problems in a specific organ include, but are not limited to, increased acidity, presence of at least one bacterium, presence of at least one virus, and imbalance of yeast.

In one embodiment, the server platform includes a proprietary element library. The element library includes biosignature data for different types of food and other elements mentioned before. The server platform is operable to update the element library with new elements introduced to the market. In one embodiment, the server platform comprises a modeling engine operable to build a virtual element based on a machine learning algorithm. The machine learning algorithm is operable to continuously extract data regarding new elements from various database and/or data sources. The modeling engine is operable to automatically build a virtual element based on collected data. In another embodiment, the modeling engine is operable to build a virtual element based on data input by a user via a GUI. In one embodiment, the server platform is operable to access to a third-party element library via an API.

In one embodiment, the server platform comprises a classification engine operable to classify the historical data and incoming data from tested subjects. The classification is based on gender, age range, race, organs, etc.

In one embodiment, the server platform comprises a reasoning engine built with artificial intelligence (AI) algorithms. The reasoning engine is operable to generate a reasoning model based on multiple sets of training data. The multiple sets of training data are a subset of historical data. For example, a subject's health condition is significantly improved after a specific treatment for a predetermined period of time. The training data includes context data (e.g., baseline data, testing data) and action data (e.g., treatment data). The reasoning model is updated periodically when there is an anomaly indicated in the action data produced by the reasoning data based on the context data. Each of U.S. Pat. No. 9,922,286 titled "Detecting and Correcting Anomalies in Computer-Based Reasoning Systems" and U.S. application Ser. No. 15/900,398 is incorporated herein by reference in its entirety.

In another embodiment, the AI algorithms are operable to detect variations in pressure applied by a practitioner during a session and across multiple sessions (e.g., single subject with multiple sessions, multiple subjects). In yet another embodiment, the AI algorithms are operable to detect variations in an angle of the probe. Pressure applied by the practitioner and the angle of the probe can both affect the conductivity readings. Advantageously, this allows the AI algorithms to detect and address bias both within a session for a single subject and over time with multiple subjects. For example, the AI algorithms are operable to detect if the practitioner tends to lower the angle of the probe towards the end of sessions for all subjects, indicating that the practitioner is fatigued and/or not focused after 45 minutes. Additionally, AI algorithms are operable to address differences in hydration determined via a hydration sensor of a single subject within a single session or for a single subject or multiple subjects over multiple sessions. In another embodiment, AI algorithms detect and account for differences in moisture or salinity at the contact point between the band electrode and the skin of a single subject over one session or multiple sessions or for multiple subjects over multiple sessions.

In one embodiment, the reasoning model is operable to generate a treatment plan for a subject based on the test results. The test results include organ reports and element test reports. The organ reports include conductivity readings for organs and identified problems for organs with conductivity readings greater than 50. The element test reports include conductivity readings and biometric index scores corresponding to different types of elements (e.g., food, food component, beverage, supplement, medication, drug, herb, spice, vitamin, mineral, gemstone, metal, electronic device, bodily fluid, tissue, hair sample).

In one embodiment, the server platform comprises an optimization engine to optimize an overall treatment plan for a subject to get maximum effectiveness when more than one problem organ is detected so that the treatment plan is good for all the problem organs, or at least certain treatments good for one problem organ do not worsen other problem organs.

Figure 7A:
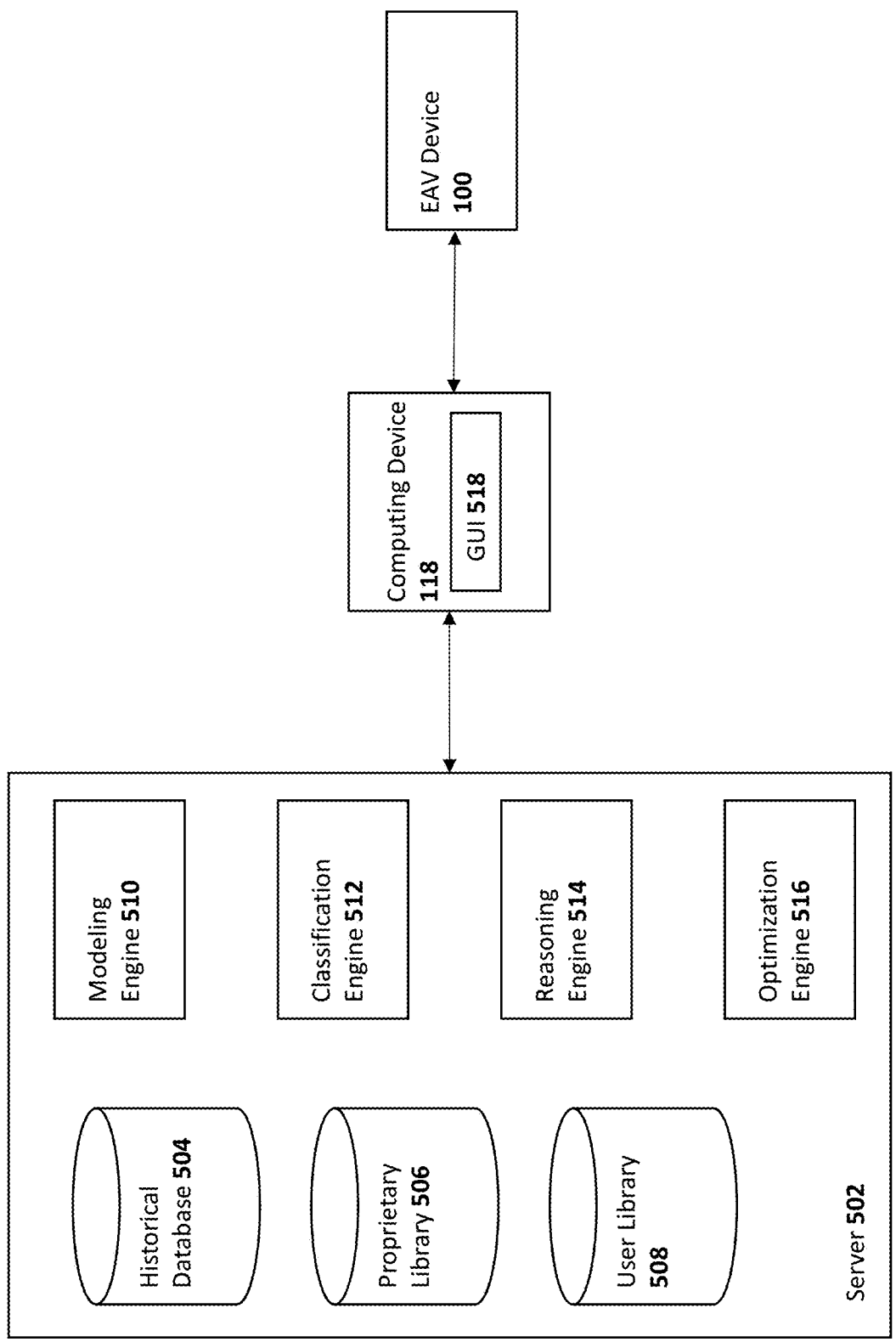
FIG. 7A is a diagram of a server platform in network communication with an EAV device via a computing device according to one embodiment of the present invention.

FIG. 7A is a diagram of a server platform 502 in network communication with an EAV device 100 via a computing device 118 according to one embodiment of the present invention. The server 502 incudes a historical database 504, a proprietary library 506, a user library 508, a modeling engine 510, a classification engine 512, a reasoning engine 514, and an optimization engine 516. The computing device 118 includes a GUI 518.

Figure 7B:
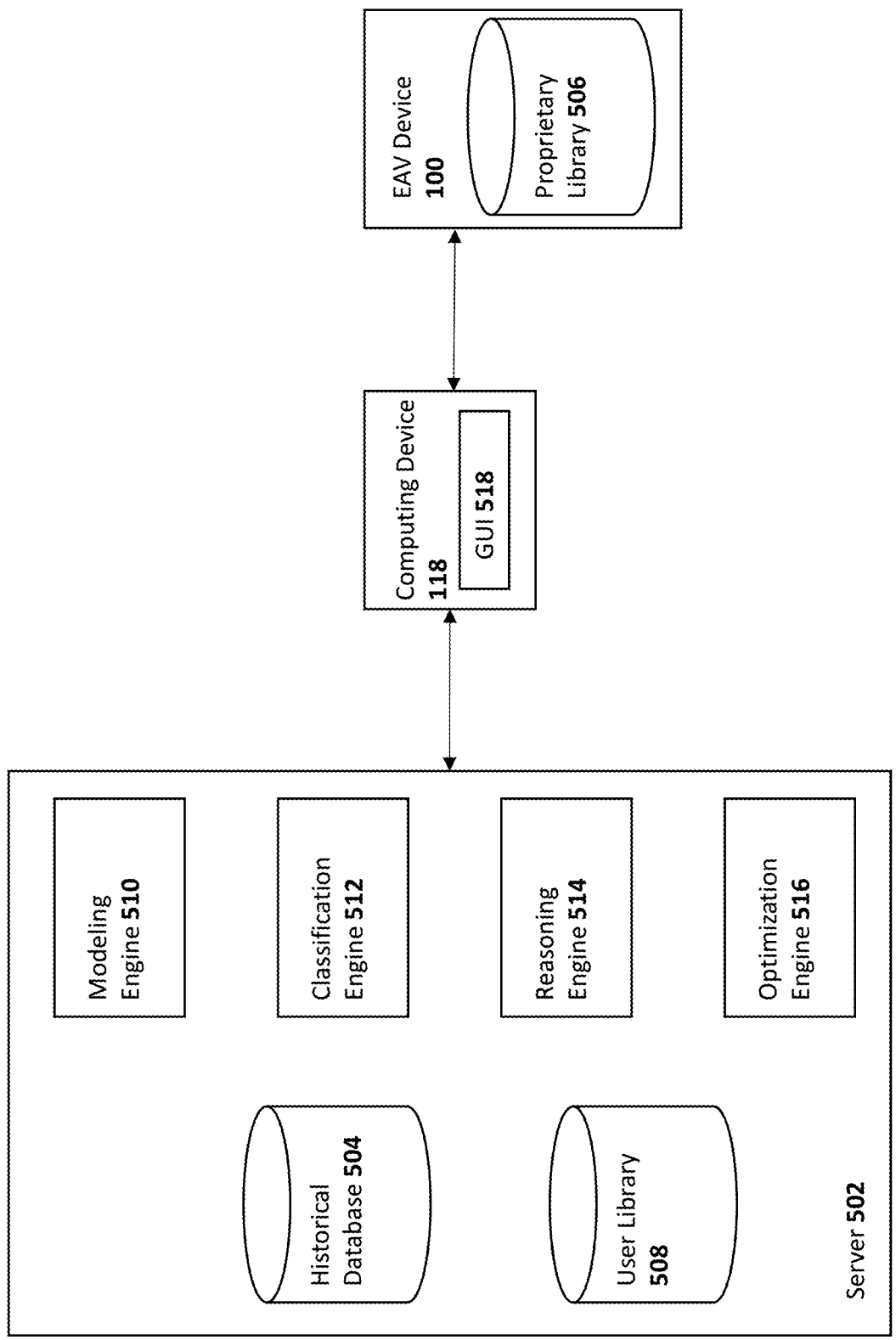
FIG. 7B is a diagram of a server platform in network communication with an EAV device via a computing device according to one embodiment of the present invention.

FIG. 7B is a diagram of a server platform 502 in network communication with an EAV device 100 via a computing device 118 according to another embodiment of the present invention. FIG. 7B differs from FIG. 7A in that the proprietary library 506 is on the EAV device 100 rather than on the server 502.

Figure 8:
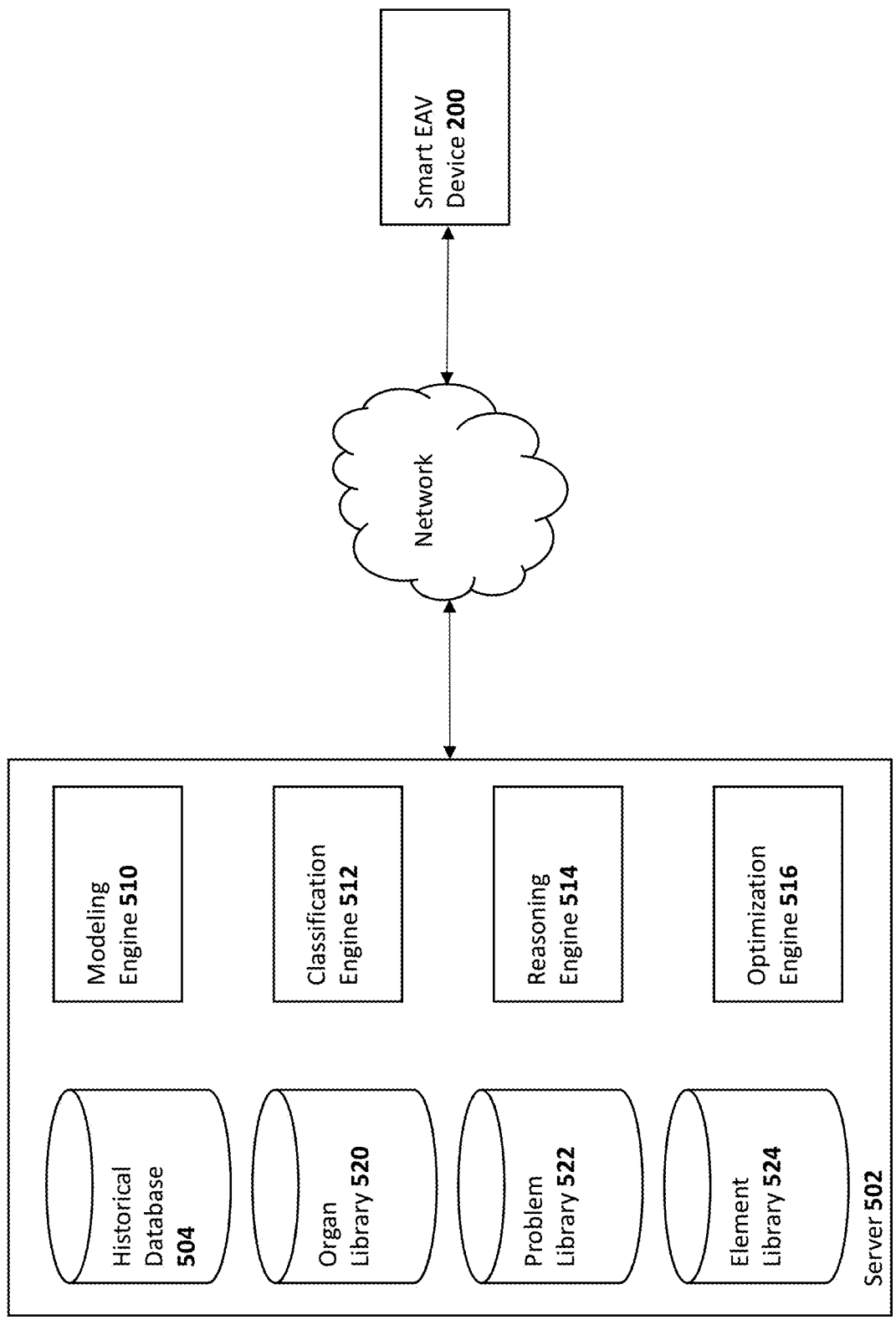
FIG. 8 is a diagram of a server platform in network communication with a computing device configured as a smart EAV device according to one embodiment of the present invention.

FIG. 8 is a diagram of a server platform 502 in network communication with a computing device configured as a smart EAV device 200 according to one embodiment of the present invention. The server 502 incudes a historical database 504, an organ library 520, a problem library 522, an element library 524, a modeling engine 510, a classification engine 512, a reasoning engine 514, and an optimization engine 516.

In one embodiment, the server platform is operable to automatically scan each subsystem of a subject based on the organ library and generate an organ report for the subject. The organ report includes conductivity readings for all organs. Problem organs are identified with conductivity readings larger than a threshold. In one embodiment, the threshold is 50, 55, 60, 65, or 70. Potential problems are identified for the problem organs as well. The server platform is also operable to automatically test a category of elements based on the element library and generate an element test report. The element test report comprises conductivity readings and biometric index scores corresponding to the test elements, comparing to the baseline conductivity reading and baseline biometric index score of the subject.

In one embodiment, the server platform is operable to generate a treatment report based on the organ report and the element test report of a subject. The treatment report includes elements good for the subject and elements to be avoided and/or limited by the subject.

In another embodiment, the server platform is operable to generate a progress report. The progress report displays historical changes in the organ report and/or the element test report over time.

In one embodiment, the server platform provides licensed access via API. An application program is downloaded and installed on a computing device. A user account is created based on the type of the user (e.g., enterprise, practitioner, and individuals). User identification is required for performing tests and accessing to historical data of the user. In one embodiment, biometric data is used for user authentication, for example, facial features, fingerprints, voices, heartbeats, vein recognition, etc. In another embodiment, a password is used for user authentication.

Figure 9:
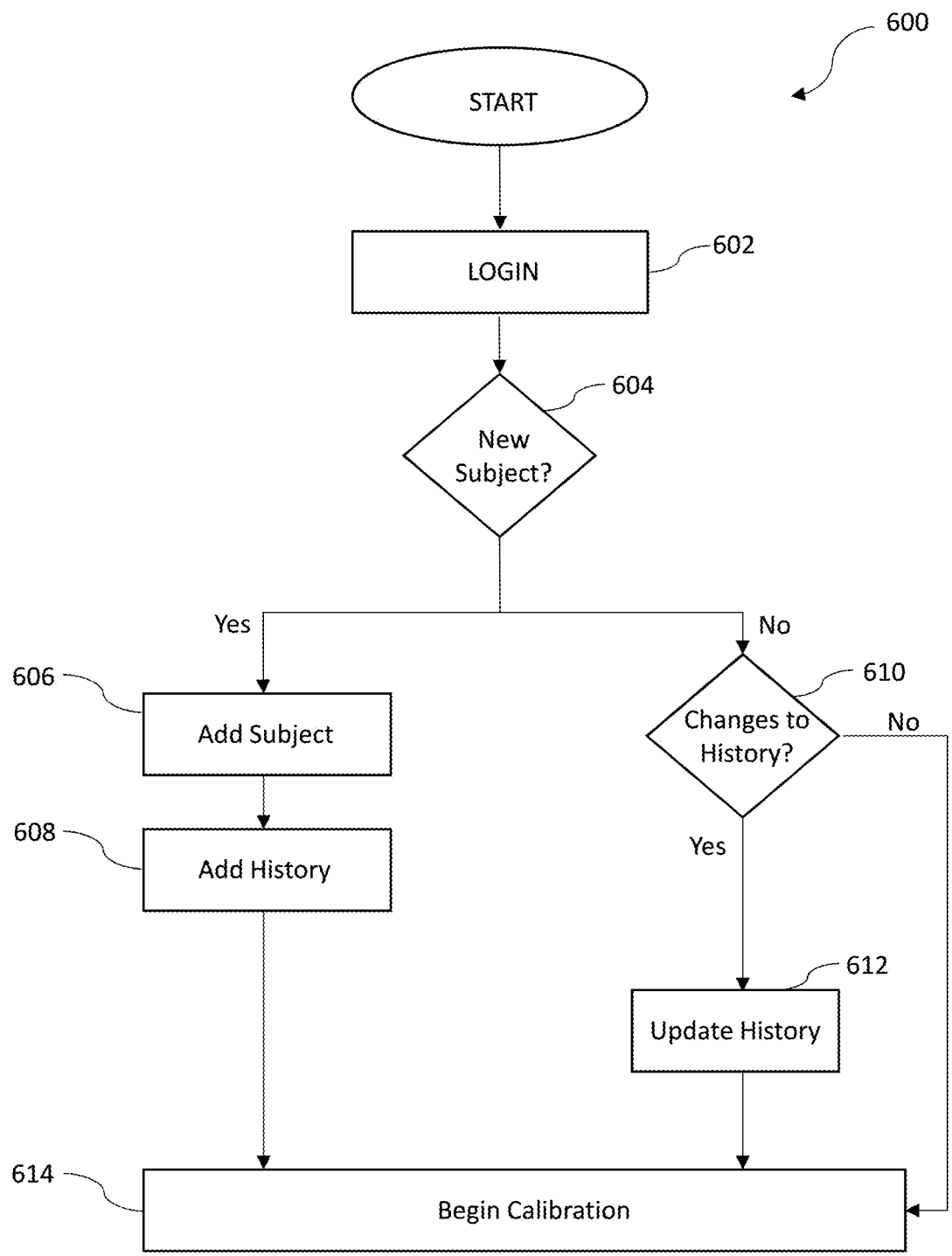
FIG. 9 is a flow chart detailing a method of logging into the server platform and updating subject information according to one embodiment of the present invention.

FIG. 9 is a flow chart detailing a method 600 of logging into the server platform and updating subject information. The user logs into the server platform in step 602. It is determined whether the subject is a new subject in step 604. If the subject is a new subject, the new subject is added to the database in step 606. A history for the new subject is added to the database in step 608 and the user begins calibration in step 614. If the subject is not a new subject, it is determined whether there are changes to a history for the subject in step 610. If there are changes to the history for the subject, the history is updated in step 612 before the user begins calibration in step 614. If there are not changes to the history in step 610, the user begins calibration in step 614.

The server platform is preferably operable to automatically transmit at least one report to the subject. Additionally, the server platform is operable to bill the subject and create appointments.

In one embodiment, the application program installed on a mobile device is operable to calculate a compatibility score of an element, an electromagnetic wave, a mechanical wave, an odor including one or more volatized chemical compounds, and combinations thereof for a specific user based on historical data stored. In one embodiment, the compatibility score indicates a degree of effectiveness, a degree of sensitivity, a degree of tolerance, and/or a tendency to toxicity for the specific user, each of which is in a range between 0 and 4. In one example, wild salmon is given a degree of effectiveness of 4 and farmed salmon is given a degree of effectiveness of 2 because the ratio of Omega-3: Omega-6 is higher in wild salmon than farmed salmon. In another example, food sensitives are given a range between 0 and 4, wherein 0 indicates no food sensitivity, 1 indicates a food sensitivity, and 4 indicates highly allergic. In one embodiment, the score is in a range between −7 and 17 by weighing the effectiveness, sensitivity, tolerance, and toxicity. In another embodiment, the score is in a range between −7 and 19. In yet another embodiment, the score is in a range between −10 and 20. The higher the score is, the better it is for the specific user. Negative scores indicate potential damage and/or threats to a specific user. For example, pain relievers harm the kidneys, even though they are effective to reduce pain. In one example, a toxic element is given a score of −2, an average remedy is given a score of between 4 and 7, and an excellent remedy is given a score of between 10 and 19. The application program is operable to recognize the elements with a barcode scan or through image recognition via the mobile device.

In one embodiment, the server platform provides training programs for users. A user accesses the training programs by logging in to their account. In one embodiment, the training program is a pre-recorded demonstration or tutorial. In another embodiment, the training program is AI-powered and operable to verbally instruct a user for a testing step by step. The training program provides test reproducibility and enables mass adoption.

Figure 10:
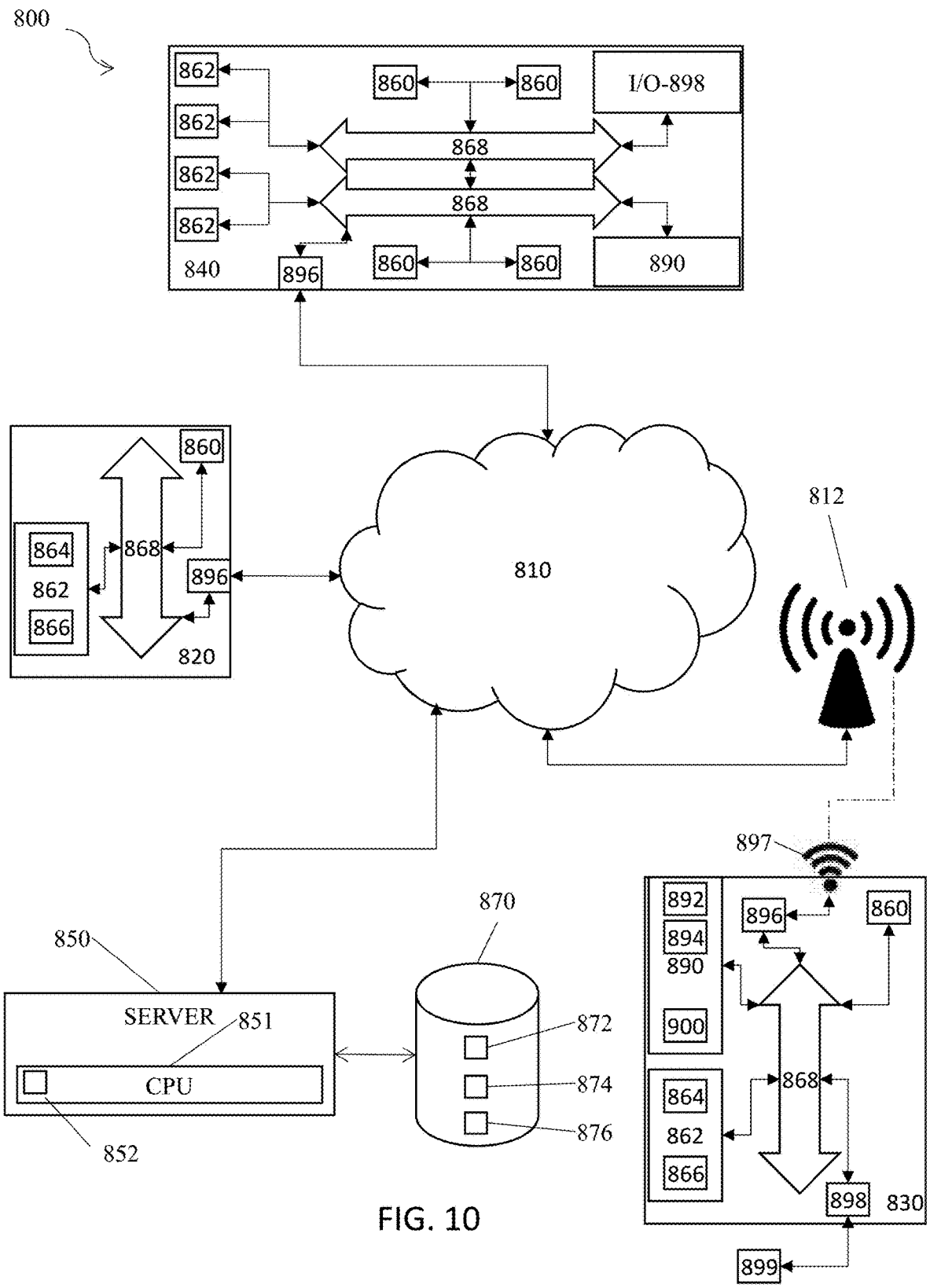
FIG. 10 is a schematic diagram of a cloud-based system of the present invention according to one embodiment of the present invention.

FIG. 10 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 may house an operating system 872, memory 874, and programs 876.

In one embodiment of the invention, the system 800 includes a cloud-based network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in this document In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. The input/output controller 898 may receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 10, multiple processors 860 and/or multiple buses 868 may be used, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multi-processor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to a bus 868. Computing devices may communicate communication media through wired networks, direct-wired connections or wirelessly, such as acoustic, RF, or infrared, through an antenna 897 in communication with the network antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications, or other data embodying any one or more of the methodologies or functions described herein. The computer readable medium may include the memory 862, the processor 860, and/or the storage media 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

It is also contemplated that the computer system 800 may not include all of the components shown in FIG. 10, may include other components that are not explicitly shown in FIG. 10, or may utilize an architecture completely different than that shown in FIG. 10. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

The above-mentioned examples are provided to serve the purpose of clarifying the aspects of the invention, and it will be apparent to one skilled in the art that they do not serve to limit the scope of the invention. By way of example, the EAV device can be a traditional EAV device or a smart EAV device. By nature, this invention is highly adjustable, customizable and adaptable. The above-mentioned examples are just some of the many configurations that the mentioned components can take on. All modifications and improvements have been deleted herein for the sake of conciseness and readability but are properly within the scope of the present invention.

What is claimed is:

1. A system for measuring galvanic skin response, comprising:
    an electrical conductivity meter electrically connected to a positive electrode and a negative electrode; and
    wherein the electrical conductivity meter includes at least one processor and at least one memory;
    wherein the negative electrode is configured to be in contact with a first portion of a subject and wherein the positive electrode is configured to be in contact with a second portion of the subject, thereby creating a circuit including the positive electrode, the negative electrode, and the subject;
    wherein the electrical conductivity meter is configured to measure the galvanic skin response of the subject;
    wherein the circuit further includes a substance in contact with a test plate of the electrical conductivity meter, and wherein the test plate includes the substance has been or is currently exposed to a stimulus;
    wherein the substance includes food, a food component, a coloring, an additive, a preservative, a thickener, a stabilizer, an emulsifier, an enhancer, a beverage, a supplement, a medication, a drug, an herb, a spice, a vitamin, a mineral, a gemstone, a metal, an electronic device, a bodily fluid, a tissue, and/or a hair sample.

2. The system of claim 1, further comprising a device including a photon source and/or a Tesla coil, wherein the device including the photon source and/or the Tesla coil is configured to expose the substance to the stimulus, and wherein the stimulus includes electromagnetic waves.

3. The system of claim 1, wherein the stimulus includes a biological output, or a resonance frequency of an animal or an organ of the animal, and wherein the biological output includes heartbeats, brainwaves, neural oscillations, breathing patterns, and/or combinations thereof.

4. The system of claim 1, wherein the stimulus includes mechanical waves.

5. The system of claim 1, wherein the stimulus includes electromagnetic waves.

6. The system of claim 1, wherein the electrical conductivity meter is configured to determine a galvanic skin measurement of the subject when the substance exposed to the stimulus is in contact with the test plate and thereby included in the circuit, and the galvanic skin measurement of the subject when the substance exposed to the stimulus is not in contact with the test plate and thereby not included in the circuit.

7. The system of claim 1, further comprising a server platform in network communication with the electrical conductivity meter, wherein the server platform is configured to compare the galvanic skin measurement of the subject when the substance exposed to the stimulus is in contact with the test plate and thereby included in the circuit, and the galvanic skin measurement of the subject when the substance exposed to the stimulus is not in contact with the test plate and thereby not included in the circuit.

8. The system of claim 7, wherein the server platform is configured to calculate a compatibility score for the substance exposed to the stimulus and the subject based on the galvanic skin measurement of the subject when the substance exposed to the stimulus is in contact with the test plate and thereby included in the circuit, and the galvanic skin measurement of the subject when the substance exposed to the stimulus is not in contact with the test plate and thereby not included in the circuit, wherein the compatibility score indicates a degree of effectiveness, a degree of sensitivity, a degree of tolerance, and/or a tendency to toxicity of the substance exposed to the stimulus for the subject.

9. The system of claim 1, wherein the stimulus includes light.

10. The system of claim 9, wherein the light is constructed based on a biological output or a resonance frequency of an animal or an organ of the animal, and wherein the biological output includes heartbeats, brainwaves, neural oscillations, breathing patterns, and/or combinations thereof.

11. The system of claim 1, wherein the stimulus includes sound.

12. The system of claim 11, wherein the sound is constructed based on a biological output or a resonance frequency of an animal or an organ of the animal, and wherein the biological output includes heartbeats, brainwaves, neural oscillations, breathing patterns, and/or combinations thereof.

13. A system for measuring galvanic skin response, comprising:
    an electrical conductivity meter electrically connected to a positive electrode and a negative electrode; and
    wherein the electrical conductivity meter includes at least one processor and at least one memory;
    wherein the positive electrode and the negative electrode are configured to create a circuit with the subject and a substance which has been or is currently exposed to a stimulus;
    wherein the electrical conductivity meter is configured to measure the galvanic skin response of a subject; and
    wherein the substance includes food, a food component, a coloring, an additive, a preservative, a thickener, a stabilizer, an emulsifier, an enhancer, a beverage, a supplement, a medication, a drug, an herb, a spice, a vitamin, a mineral, a gemstone, a metal, an electronic device, a bodily fluid, a tissue, and/or a hair sample.

14. The system of claim 13, wherein the stimulus includes a biological output, or a resonance frequency of an animal or an organ of the animal, and wherein the biological output includes heartbeats, brainwaves, neural oscillations, breathing patterns, and/or combinations thereof.

15. The system of claim 13, wherein the stimulus includes light.

16. The system of claim 15, wherein the light is constructed based on a biological output or a resonance frequency of an animal or an organ of the animal, and wherein the biological output includes heartbeats, brainwaves, neural oscillations, breathing patterns, and/or combinations thereof.

17. The system of claim 13, wherein the stimulus includes sound.

18. The system of claim 17, wherein the sound is constructed based on a biological output or a resonance frequency of an animal or an organ of the animal, and wherein the biological output includes heartbeats, brainwaves, neural oscillations, breathing patterns, and/or combinations thereof.

19. A system for measuring galvanic skin response, comprising:
- an electrical conductivity meter electrically connected to a positive electrode and a negative electrode; and
- wherein the electrical conductivity meter includes at least one processor and at least one memory;
- wherein the positive electrode and the negative electrode are configured to create a circuit with the subject;
- wherein the electrical conductivity meter is configured to measure the galvanic skin response of a subject; and
- wherein a substance is exposed to electromagnetic and/or mechanical waves during the measurement of the galvanic skin response of the subject.

20. The system of claim 19, wherein the electromagnetic and/or mechanical waves are based on a biological output, or a resonance frequency of an animal or an organ of the animal, and wherein the biological output includes heartbeats, brainwaves, neural oscillations, breathing patterns, and/or combinations thereof.

* * * * *